US008870866B2

(12) United States Patent
Woloszko

(10) Patent No.: US 8,870,866 B2
(45) Date of Patent: Oct. 28, 2014

(54) ELECTROSURGICAL SYSTEM WITH SUCTION CONTROL APPARATUS, SYSTEM AND METHOD

(75) Inventor: Jean Woloszko, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 159 days.

(21) Appl. No.: 13/457,654

(22) Filed: Apr. 27, 2012

(65) Prior Publication Data

US 2012/0215221 A1 Aug. 23, 2012

Related U.S. Application Data

(62) Division of application No. 11/969,283, filed on Jan. 4, 2008, now Pat. No. 8,192,424.

(60) Provisional application No. 60/883,698, filed on Jan. 5, 2007.

(51) Int. Cl.

| | |
|---|---|
| ***A61B 18/18*** | (2006.01) |
| ***A61B 18/12*** | (2006.01) |
| *A61B 18/14* | (2006.01) |
| *A61B 18/00* | (2006.01) |

(52) U.S. Cl.

CPC ....... *A61B 18/1206* (2013.01); *A61B 2218/007* (2013.01); *A61B 2018/1472* (2013.01); *A61B 2218/002* (2013.01); *A61B 2018/0016* (2013.01)

USPC ............................................ 606/50; 606/41

(58) Field of Classification Search

CPC ............................... A61B 18/12; A61B 18/14

USPC .................................................... 606/32–45

See application file for complete search history.

(56) References Cited

U.S. PATENT DOCUMENTS

| | | | | |
|---|---|---|---|---|
| 2,050,904 | A | 4/1936 | Trice | 219/31 |
| 2,056,377 | A | 10/1939 | Wappler | 125/303 |

(Continued)

FOREIGN PATENT DOCUMENTS

| | | | |
|---|---|---|---|
| DE | 3119735 | 1/1983 | A61B 17/39 |
| DE | 3930451 A1 | 3/1991 | A61B 17/39 |

(Continued)

OTHER PUBLICATIONS

Buchelt, et al. "Excimer Laser Ablation of Fibrocartilage: An in Vitro and in Vivo Study", Lasers in Surgery and Medicine, vol. 11, pp. 271-279, 1991.

(Continued)

*Primary Examiner* — Linda Dvorak
*Assistant Examiner* — Amanda Scott
(74) *Attorney, Agent, or Firm* — Matthew Scheele; Brian E. Szymczak

(57) ABSTRACT

System and method for selectively applying electrical energy to structures within or on the surface of a patient's body and controlling the flow of an electrically conductive fluid from the application site to provide or maintain a desired operating condition of the electrosurgical device. An electrosurgical probe is in communication with a fluid transport apparatus through a fluid transport lumen having an opening at an end proximate the application site and disposed proximate the electrosurgical probe. A controller in communication with the fluid transport apparatus provides control signals to the fluid transport apparatus in response to at least one operating parameter associated with the system. Based on the received control signals, the fluid transport apparatus adjusts a flow rate of the electrically conductive fluid at the application site through the fluid transport lumen in response to at least one operating parameter associated with the system.

27 Claims, 7 Drawing Sheets

(56) References Cited

U.S. PATENT DOCUMENTS

| | | | | |
|---|---|---|---|---|
| 2,611,365 | A | 9/1952 | Rubens | 606/42 |
| 3,434,476 | A | 3/1969 | Shaw et al. | 606/22 |
| 3,633,425 | A | 1/1972 | Sanford | 73/356 |
| 3,707,149 | A | 12/1972 | Hao et al. | 128/303.14 |
| 3,718,617 | A | 2/1973 | Royal | 260/30.4 |
| 3,815,604 | A | 6/1974 | O'Malley et al. | 128/305 |
| 3,828,780 | A | 8/1974 | Morrison, Jr. et al. | 128/275 |
| 3,901,242 | A | 8/1975 | Storz | 128/303 |
| 3,920,021 | A | 11/1975 | Hiltebrandt | 128/303 |
| 3,939,839 | A | 2/1976 | Curtiss | 128/303 |
| 3,963,030 | A | 6/1976 | Newton | 606/40 |
| 3,964,487 | A | 6/1976 | Judson | 606/39 |
| 3,970,088 | A | 7/1976 | Morrison | 128/303 |
| 4,033,351 | A | 7/1977 | Hetzel | 606/48 |
| 4,040,426 | A | 8/1977 | Morrison, Jr. | 128/303 |
| 4,043,342 | A | 8/1977 | Morrison, Jr. | 128/303 |
| 4,074,718 | A | 2/1978 | Morrison, Jr. | 128/303 |
| 4,092,986 | A | 6/1978 | Schneiderman | 128/303 |
| D249,549 | S | 9/1978 | Pike | D24/144 |
| 4,114,623 | A | 9/1978 | Meinke et al. | 606/39 |
| 4,116,198 | A | 9/1978 | Roos | 128/303 |
| 4,181,131 | A | 1/1980 | Ogiu | 128/303 |
| 4,184,492 | A | 1/1980 | Meinke et al. | 128/303 |
| 4,202,337 | A | 5/1980 | Hren et al. | 128/303 |
| 4,228,800 | A | 10/1980 | Degler, Jr. et al. | 128/303 |
| 4,232,676 | A | 11/1980 | Herczog | 128/303 |
| 4,240,441 | A | 12/1980 | Khalil | 600/505 |
| 4,248,231 | A | 2/1981 | Herczog et al. | 128/303 |
| 4,301,801 | A | 11/1981 | Schneiderman | 606/38 |
| 4,326,529 | A | 4/1982 | Doss et al. | 128/303 |
| 4,346,715 | A | 8/1982 | Gammell | 607/99 |
| 4,363,324 | A | 12/1982 | Kusserow | 607/64 |
| 4,378,801 | A | 4/1983 | Oosten | 606/37 |
| 4,381,007 | A | 4/1983 | Doss | 128/303 |
| 4,418,692 | A | 12/1983 | Guay | 606/42 |
| 4,474,179 | A | 10/1984 | Koch | 606/40 |
| 4,476,862 | A | 10/1984 | Pao | 128/303 |
| 4,509,532 | A | 4/1985 | DeVries | 128/736 |
| 4,520,818 | A | 6/1985 | Mickiewicz | 606/40 |
| 4,532,924 | A | 8/1985 | Auth et al. | 128/303 |
| 4,548,207 | A | 10/1985 | Reimels | 128/303 |
| 4,567,890 | A | 2/1986 | Ohta et al. | 128/303 |
| 4,572,206 | A | 2/1986 | Geddes et al. | 600/505 |
| 4,580,557 | A | 4/1986 | Hertzmann | 606/12 |
| 4,587,975 | A | 5/1986 | Salo et al. | 600/506 |
| 4,590,934 | A | 5/1986 | Malis et al. | 128/303 |
| 4,593,691 | A | 6/1986 | Lindstrom et al. | 128/303 |
| 4,658,817 | A | 4/1987 | Hardy | 606/14 |
| 4,660,571 | A | 4/1987 | Hess et al. | 128/784 |
| 4,674,499 | A | 6/1987 | Pao | 128/303 |
| 4,682,596 | A | 7/1987 | Bales et al. | 128/303 |
| 4,706,667 | A | 11/1987 | Roos | 128/303 |
| 4,709,698 | A | 12/1987 | Johnston et al. | 606/41 |
| 4,727,874 | A | 3/1988 | Bowers et al. | 128/303 |
| 4,750,902 | A | 6/1988 | Wuchinich et al. | 604/22 |
| 4,765,331 | A | 8/1988 | Petruzzi et al. | 128/303 |
| 4,785,823 | A | 11/1988 | Eggers et al. | 128/692 |
| 4,805,616 | A | 2/1989 | Pao | 128/303 |
| 4,823,791 | A | 4/1989 | D'Amelio et al. | 123/303 |
| 4,832,048 | A | 5/1989 | Cohen | 128/786 |
| 4,846,179 | A | 7/1989 | O'Connor | 607/72 |
| 4,860,752 | A | 8/1989 | Turner | 607/102 |
| 4,898,169 | A | 2/1990 | Norman et al. | 606/42 |
| 4,907,589 | A | 3/1990 | Cosman | 606/34 |
| 4,920,978 | A | 5/1990 | Colvin | 128/784 |
| 4,931,047 | A | 6/1990 | Broadwin et al. | 604/22 |
| 4,936,281 | A | 6/1990 | Stasz | 128/660 |
| 4,936,301 | A | 6/1990 | Rexroth et al. | 606/45 |
| 4,943,290 | A | 7/1990 | Rexroth et al. | 606/45 |
| 4,955,377 | A | 9/1990 | Lennox et al. | 607/105 |
| 4,966,597 | A | 10/1990 | Cosman | 606/50 |
| 4,967,765 | A | 11/1990 | Turner et al. | 128/785 |
| 4,976,711 | A | 12/1990 | Parins et al. | 606/48 |
| 4,979,948 | A | 12/1990 | Geddes et al. | 606/33 |
| 4,998,933 | A | 3/1991 | Eggers et al. | 606/41 |
| 5,007,908 | A | 4/1991 | Rydell | 606/47 |
| 5,009,656 | A | 4/1991 | Reimels | 606/48 |
| 5,026,387 | A | 6/1991 | Thomas | 606/169 |
| 5,035,696 | A | 7/1991 | Rydell | 606/47 |
| 5,047,026 | A | 9/1991 | Rydell | 606/48 |
| 5,047,027 | A | 9/1991 | Rydell | 606/48 |
| 5,057,105 | A | 10/1991 | Malone et al. | 606/28 |
| 5,057,106 | A | 10/1991 | Kasevich et al. | 606/33 |
| 5,078,717 | A | 1/1992 | Parins et al. | 606/48 |
| 5,080,660 | A | 1/1992 | Buelna | 606/45 |
| 5,083,565 | A | 1/1992 | Parins et al. | 600/374 |
| 5,084,044 | A | 1/1992 | Quint | 606/27 |
| 5,085,659 | A | 2/1992 | Rydell | 606/47 |
| 5,088,997 | A | 2/1992 | Delahuerga et al. | 606/42 |
| 5,092,339 | A | 3/1992 | Geddes et al. | 606/505 |
| 5,098,431 | A | 3/1992 | Rydell | 606/48 |
| 5,099,840 | A | 3/1992 | Goble | 128/422 |
| 5,102,410 | A | 4/1992 | Dressel | 606/15 |
| 5,108,391 | A | 4/1992 | Flachenecker et al. | 606/38 |
| RE33,925 | E | 5/1992 | Bales et al. | 606/48 |
| 5,112,330 | A | 5/1992 | Nishigaki et al. | 606/46 |
| 5,122,138 | A | 6/1992 | Manwaring | 606/46 |
| 5,125,928 | A | 6/1992 | Parins et al. | 606/48 |
| 5,156,151 | A | 10/1992 | Imran | 600/375 |
| 5,167,659 | A | 12/1992 | Ohtomo et al. | 606/40 |
| 5,171,311 | A | 12/1992 | Rydell et al. | 606/48 |
| 5,174,304 | A | 12/1992 | Latina et al. | 607/141 |
| 5,178,620 | A | 1/1993 | Eggers et al. | 606/41 |
| 5,183,338 | A | 2/1993 | Wickersheim et al. | 374/131 |
| 5,190,517 | A | 3/1993 | Zieve et al. | 604/22 |
| 5,192,280 | A | 3/1993 | Parins | 606/48 |
| 5,195,959 | A | 3/1993 | Smith | 604/34 |
| 5,197,466 | A | 3/1993 | Marchosky et al. | 128/399 |
| 5,197,963 | A | 3/1993 | Parins | 606/46 |
| 5,207,675 | A | 5/1993 | Canady | 606/40 |
| 5,217,457 | A | 6/1993 | Delahuerga et al. | 606/42 |
| 5,217,459 | A | 6/1993 | Kamerling | 606/48 |
| 5,249,585 | A | 10/1993 | Turner et al. | 607/99 |
| 5,255,980 | A | 10/1993 | Thomas et al. | 374/161 |
| 5,261,410 | A | 11/1993 | Alfano et al. | 600/475 |
| 5,267,994 | A | 12/1993 | Gentelia et al. | 606/15 |
| 5,267,997 | A | 12/1993 | Farin et al. | 606/38 |
| 5,273,524 | A | 12/1993 | Fox et al. | 604/21 |
| 5,277,201 | A | 1/1994 | Stern | 607/98 |
| 5,281,216 | A | 1/1994 | Klicek | 606/42 |
| 5,281,218 | A | 1/1994 | Imran | 606/41 |
| 5,282,799 | A | 2/1994 | Rydell | 606/48 |
| 5,290,282 | A | 3/1994 | Casscells | 606/29 |
| 5,300,069 | A | 4/1994 | Hunsberger et al. | 606/37 |
| 5,306,238 | A | 4/1994 | Fleenor | 606/42 |
| 5,312,400 | A | 5/1994 | Bales et al. | 606/41 |
| 5,314,406 | A | 5/1994 | Arias et al. | 604/21 |
| 5,318,563 | A | 6/1994 | Malis et al. | 606/38 |
| 5,324,254 | A | 6/1994 | Phillips | 604/21 |
| 5,330,470 | A | 7/1994 | Hagen | 606/42 |
| 5,334,140 | A | 8/1994 | Philips | 604/35 |
| 5,334,183 | A | 8/1994 | Wuchinich | 606/46 |
| 5,334,193 | A * | 8/1994 | Nardella | 606/41 |
| 5,336,172 | A | 8/1994 | Bales et al. | 604/27 |
| 5,336,220 | A | 8/1994 | Ryan et al. | 604/22 |
| 5,336,443 | A | 8/1994 | Odashima | 252/511 |
| 5,342,357 | A | 8/1994 | Nardella | 606/40 |
| 5,348,554 | A | 9/1994 | Imran et al. | 606/41 |
| 5,354,291 | A | 10/1994 | Bales et al. | 604/35 |
| 5,366,443 | A | 11/1994 | Eggers et al. | 604/114 |
| 5,370,675 | A | 12/1994 | Edwards et al. | 607/101 |
| 5,374,261 | A | 12/1994 | Yoon | 604/385.01 |
| 5,375,588 | A | 12/1994 | Yoon | 128/4 |
| 5,380,277 | A | 1/1995 | Phillips | 604/33 |
| 5,380,316 | A | 1/1995 | Aita | 606/7 |
| 5,383,874 | A | 1/1995 | Jackson et al. | 606/1 |
| 5,383,876 | A | 1/1995 | Nardella | 606/49 |
| 5,383,917 | A | 1/1995 | Desai et al. | 607/702 |
| 5,389,096 | A | 2/1995 | Aita | 606/15 |
| 5,395,312 | A | 3/1995 | Desai | 604/22 |
| 5,400,267 | A | 3/1995 | Denen et al. | 702/59 |
| 5,401,272 | A | 3/1995 | Perkins | 606/15 |
| 5,403,311 | A | 4/1995 | Abele et al. | 606/49 |
| 5,417,687 | A | 5/1995 | Nardella et al. | 606/32 |

(56) References Cited

U.S. PATENT DOCUMENTS 5,419,767 A 5/1995 Eggers et al. ................ 604/114
5,423,810 A 6/1995 Goble et al. .................... 606/40
5,423,882 A 6/1995 Jackman et al. .............. 607/122
5,436,566 A 7/1995 Thompson et al. ........... 324/713
5,437,662 A 8/1995 Nardella ......................... 606/40
5,438,302 A 8/1995 Goble ........................... 331/167
5,441,499 A 8/1995 Fritzsch .......................... 606/45
5,449,356 A 9/1995 Walbrink et al. ............... 606/49
5,451,224 A 9/1995 Goble et al. .................... 606/48
5,454,809 A 10/1995 Janssen ........................... 606/41
5,458,596 A 10/1995 Lax et al. ........................ 606/31
5,458,597 A 10/1995 Edwards et al. ................ 606/41
5,472,443 A 12/1995 Cordis et al. .................... 606/48
5,486,161 A 1/1996 Lax et al. ........................ 604/22
5,496,312 A 3/1996 Klicek ............................ 606/34
5,496,314 A 3/1996 Eggers ............................ 606/41
5,496,317 A 3/1996 Goble et al. .................... 606/48
5,505,730 A 4/1996 Edwards ......................... 606/41
5,507,743 A 4/1996 Edwards et al. ................ 606/41
5,514,130 A 5/1996 Baker ............................. 606/41
5,540,683 A 7/1996 Ichikawa et al. ................ 606/40
5,542,915 A 8/1996 Edwards et al. ................ 604/22
5,549,598 A 8/1996 O'Donnell, Jr. .................. 606/6
5,554,152 A 9/1996 Aita .................................. 606/7
5,556,397 A 9/1996 Long et al. ...................... 606/48
5,562,703 A 10/1996 Desai ............................ 606/210
5,569,242 A 10/1996 Lax et al. ........................ 606/42
5,571,100 A 11/1996 Goble et al. .................... 606/41
5,573,533 A 11/1996 Strul ............................... 606/34
5,584,872 A 12/1996 LaFontaine et al. .......... 607/117
5,588,960 A 12/1996 Edwards et al. ................ 604/20
5,599,350 A 2/1997 Schulze et al. .................. 606/51
5,609,151 A 3/1997 Mulier et al. ................. 128/642
5,609,573 A 3/1997 Sandock ......................... 604/22
5,633,578 A 5/1997 Eggers et al. ................ 323/301
5,634,921 A 6/1997 Hood et al. ....................... 606/5
5,643,304 A 7/1997 Schechter et al. ............ 606/171
5,647,869 A 7/1997 Goble et al. .................... 606/37
5,658,278 A 8/1997 Imran et al. ..................... 606/41
5,660,567 A 8/1997 Nierlich et al. .......... 439/620.21
5,662,680 A 9/1997 Desai ............................ 606/210
5,676,693 A 10/1997 LaFontaine et al. .......... 607/116
5,681,282 A 10/1997 Eggers et al. ................ 604/114
5,683,366 A 11/1997 Eggers et al. ................ 604/114
5,697,281 A 12/1997 Eggers et al. ................ 604/114
5,697,536 A 12/1997 Eggers et al. ................ 604/114
5,697,882 A 12/1997 Eggers et al. ................ 604/114
5,697,909 A 12/1997 Eggers et al. ................ 604/114
5,697,927 A 12/1997 Imran et al. ..................... 606/41
5,700,262 A 12/1997 Acosta et al. ................... 606/48
5,715,817 A 2/1998 Stevens-Wright et al. ... 600/373
5,722,975 A 3/1998 Edwards et al. ................ 606/41
5,725,524 A 3/1998 Mulier et al. ................... 606/41
5,749,869 A 5/1998 Lindenmeier et al. .......... 606/34
5,749,871 A 5/1998 Hood et al. ...................... 606/50
5,749,914 A 5/1998 Janssen ......................... 607/116
5,755,753 A 5/1998 Knowlton ....................... 607/98
5,766,153 A 6/1998 Eggers et al. ................ 604/114
5,769,847 A 6/1998 Panescu et al. ................. 606/42
5,785,705 A 7/1998 Baker ............................. 606/32
5,786,578 A 7/1998 Christy et al. ................ 219/720
5,800,429 A 9/1998 Edwards ......................... 606/41
5,807,395 A 9/1998 Mulier et al. ................... 606/41
5,810,764 A 9/1998 Eggers et al. ................... 604/23
5,810,802 A 9/1998 Panescu et al. ................. 606/31
5,810,809 A 9/1998 Rydell ............................ 606/49
5,836,875 A 11/1998 Webster, Jr. .................. 600/374
5,836,897 A 11/1998 Sakurai et al. .................... 601/2
5,843,019 A 12/1998 Eggers et al. ................... 604/22
5,860,951 A 1/1999 Eggers .......................... 604/510
5,860,974 A 1/1999 Abele ............................. 606/41
5,860,975 A 1/1999 Goble et al. .................... 606/45
5,871,469 A 2/1999 Eggers et al. ................ 604/114
5,873,855 A 2/1999 Eggers et al. ................ 604/114
5,873,877 A 2/1999 McGaffigan et al. ........... 606/41
5,885,277 A 3/1999 Korth .............................. 606/35
5,888,198 A 3/1999 Eggers et al. ................ 604/114
5,891,095 A 4/1999 Eggers et al. ................ 604/114
5,891,134 A 4/1999 Goble et al. .................... 606/27
5,897,553 A 4/1999 Mulier ............................ 606/41
5,902,272 A 5/1999 Eggers et al. ................ 604/114
5,944,715 A 8/1999 Goble et al. .................... 606/41
5,954,716 A 9/1999 Sharkey et al. ................. 606/32
5,964,786 A 10/1999 Ochs et al. ........................ 607/5
6,004,319 A 12/1999 Goble et al. .................... 606/48
6,013,076 A 1/2000 Goble et al. .................... 606/41
6,015,406 A 1/2000 Goble et al. .................... 606/41
6,024,733 A 2/2000 Eggers et al. ................ 604/500
6,027,501 A 2/2000 Goble et al. .................... 606/41
6,039,734 A 3/2000 Goble et al. .................... 606/41
6,047,700 A 4/2000 Eggers et al. ................ 128/898
6,056,746 A 5/2000 Goble et al. .................... 606/48
6,063,079 A 5/2000 Hovda et al. .................... 606/41
6,066,134 A 5/2000 Eggers et al. ................... 606/32
6,066,489 A 5/2000 Fields et al. .................. 435/236
6,068,628 A 5/2000 Fanton et al. ................... 606/41
6,074,386 A 6/2000 Goble et al. .................... 606/34
6,086,585 A 7/2000 Hovda et al. .................... 606/45
6,090,106 A 7/2000 Goble et al. .................... 606/41
6,090,107 A 7/2000 Borgmeier et al. ............. 606/41
6,093,186 A 7/2000 Goble et al. .................... 606/34
6,102,046 A 8/2000 Weinstein et al. ............ 128/898
6,105,581 A 8/2000 Eggers et al. ................ 128/898
6,109,268 A 8/2000 Thapliyal et al. ............ 128/898
6,117,109 A 9/2000 Eggers et al. ................ 604/114
6,126,682 A 10/2000 Sharkey et al. ................. 607/96
6,135,999 A 10/2000 Fanton et al. ................... 606/45
6,142,992 A 11/2000 Cheng et al. .................... 606/34
6,149,620 A 11/2000 Baker et al. ..................... 604/22
6,156,334 A 12/2000 Meyer-Ingold et al. ...... 424/443
6,159,194 A 12/2000 Eggers et al. ................ 604/500
6,159,208 A 12/2000 Hovda et al. .................... 606/41
6,162,217 A 12/2000 Kannenberg et al. ........... 606/34
6,168,593 B1 1/2001 Sharkey et al. ................. 606/34
6,174,309 B1 1/2001 Wrublewski et al. ........... 606/45
6,179,824 B1 1/2001 Eggers et al. ................ 604/500
6,179,836 B1 1/2001 Eggers et al. ................... 606/45
6,183,469 B1 2/2001 Thapliyal et al. .............. 606/41
6,190,381 B1 2/2001 Olsen et al. ..................... 606/32
6,197,021 B1 3/2001 Panescu et al. ................. 606/31
6,203,542 B1 3/2001 Ellsberry et al. ................ 606/41
6,210,402 B1 4/2001 Olsen et al. ..................... 606/32
6,210,405 B1 4/2001 Goble et al. .................... 606/41
6,224,592 B1 5/2001 Eggers et al. ................... 606/32
6,228,078 B1 5/2001 Eggers ........................... 606/32
6,228,081 B1 5/2001 Goble ............................. 606/34
6,234,178 B1 5/2001 Goble et al. .................. 128/898
6,235,020 B1 5/2001 Cheng et al. .................... 606/34
6,237,604 B1 5/2001 Burnside et al. .............. 128/897
6,238,391 B1 5/2001 Olsen et al. ..................... 606/41
6,238,393 B1 5/2001 Mulier et al. ................... 606/41
6,241,723 B1 6/2001 Heim et al. ...................... 606/34
6,249,706 B1 6/2001 Sobota et al. ................. 607/115
6,254,600 B1 7/2001 Willink et al. ................... 606/41
6,258,087 B1 7/2001 Edwards et al. ................ 606/41
6,261,286 B1 7/2001 Goble et al. .................... 606/34
6,261,311 B1 7/2001 Sharkey et al. ................. 607/96
6,264,652 B1 7/2001 Eggers et al. ................... 606/41
6,270,460 B1 8/2001 McCartan et al. ............ 600/459
6,277,112 B1 8/2001 Underwood et al. ........... 606/32
6,280,441 B1 8/2001 Ryan .............................. 606/45
6,283,961 B1 9/2001 Underwood et al. ........... 604/41
6,293,942 B1 9/2001 Goble et al. .................... 606/38
6,296,636 B1 10/2001 Cheng et al. .................... 606/32
6,296,638 B1 10/2001 Davison et al. ................. 606/41
6,306,134 B1 10/2001 Goble et al. .................... 606/42
6,308,089 B1 10/2001 von der Rur et al. ......... 600/338
6,309,387 B1 10/2001 Eggers et al. ................... 606/41
6,312,408 B1 11/2001 Eggers et al. ................ 604/114
6,319,007 B1 11/2001 Livaditis ....................... 433/224
6,322,549 B1 11/2001 Eggers et al. ................ 604/500
6,346,104 B2 2/2002 Daly et al. ...................... 606/34
6,346,107 B1 2/2002 Cucin ............................. 606/49
6,355,032 B1 3/2002 Hovda et al. .................... 606/32

(56) References Cited

U.S. PATENT DOCUMENTS 6,363,937 B1 4/2002 Hovda et al. .................. 128/898
6,364,877 B1 4/2002 Goble et al. .................... 606/34
6,379,350 B1 4/2002 Sharkey et al. ................. 606/41
6,379,351 B1 4/2002 Thapliyal et al. ............... 606/41
6,391,025 B1 5/2002 Weinstein et al. .............. 606/41
6,409,722 B1 6/2002 Hoey et al. ...................... 606/34
6,416,507 B1 7/2002 Eggers et al. ................... 606/32
6,416,508 B1 7/2002 Eggers et al. ................... 606/32
6,416,509 B1 7/2002 Goble et al. .................... 606/37
6,425,912 B1 7/2002 Knowlton ..................... 607/101
6,432,103 B1 8/2002 Ellsberry et al. ................ 606/41
6,440,129 B1 8/2002 Simpson ......................... 606/42
6,468,274 B1 10/2002 Alleyne et al. ................. 606/32
6,468,275 B1 10/2002 Wampler et al. ................ 606/48
6,482,201 B1 11/2002 Olsen et al. ..................... 606/41
6,514,248 B1 2/2003 Eggers et al. ................... 606/41
6,514,250 B1 2/2003 Jahns et al. ..................... 606/41
6,517,498 B1 2/2003 Burbank et al. .............. 600/564
6,530,922 B2 3/2003 Cosman .......................... 606/34
6,558,382 B2 5/2003 Jahns et al. ..................... 606/41
6,565,560 B1 5/2003 Goble et al. .................... 606/41
6,578,579 B2 6/2003 Burnside ....................... 128/897
6,589,237 B2 7/2003 Woloszko et al. .............. 606/41
6,602,248 B1 8/2003 Sharps et al. ................... 606/32
6,620,156 B1 9/2003 Garito et al. .................... 606/50
6,632,193 B1 10/2003 Davison et al. ................. 604/22
6,632,220 B1 10/2003 Eggers et al. ................... 606/41
6,635,034 B1 * 10/2003 Cosmescu ..................... 604/289
6,640,128 B2 10/2003 Vilsmeier et al. ............. 600/427
6,656,177 B2 12/2003 Truckai et al. .................. 606/51
6,663,554 B2 12/2003 Babaev ............................. 600/2
6,663,627 B2 12/2003 Francischelli et al. .......... 606/41
6,702,810 B2 3/2004 McClurken et al. ............ 606/34
6,730,080 B2 5/2004 Harano et al. .................. 606/38
6,746,447 B2 6/2004 Davison et al. ................. 606/41
6,749,604 B1 6/2004 Eggers et al. ................... 606/41
6,749,608 B2 6/2004 Garito et al. .................... 606/45
D493,530 S 7/2004 Reschke ...................... D24/144
6,770,071 B2 8/2004 Woloszko et al. .............. 606/41
6,780,178 B2 8/2004 Palanker et al. ................ 600/41
6,780,180 B1 8/2004 Goble et al. .................... 606/41
6,780,184 B2 8/2004 Tanrisever ...................... 606/45
6,802,842 B2 10/2004 Ellman et al. ................... 606/45
6,837,887 B2 1/2005 Woloszko et al. .............. 606/41
6,837,888 B2 1/2005 Ciarrocca et al. ............... 606/41
6,864,686 B2 3/2005 Novak et al. .................. 324/419
6,866,671 B2 3/2005 Tierney et al. ................ 606/130
6,872,183 B2 3/2005 Sampson et al. .............. 600/561
6,878,149 B2 4/2005 Gatto .............................. 606/46
6,890,307 B2 5/2005 Kokate et al. ................. 600/549
6,892,086 B2 5/2005 Russell ......................... 600/372
6,911,027 B1 6/2005 Edwards et al. ................ 606/40
6,920,883 B2 7/2005 Bessette et al. ............... 128/898
6,921,398 B2 7/2005 Carmel et al. .................. 606/41
6,929,640 B1 8/2005 Underwood et al. ........... 606/32
6,949,096 B2 9/2005 Davison et al. ................. 606/41
6,953,461 B2 10/2005 McClurken et al. ............ 606/51
6,960,204 B2 11/2005 Eggers et al. ................... 606/32
6,974,453 B2 12/2005 Woloszko et al. .............. 606/41
6,979,328 B2 12/2005 Baerveldt et al. ................. 606/6
6,979,601 B2 12/2005 Marr et al. .................... 438/132
6,984,231 B2 1/2006 Goble et al. .................... 606/37
6,986,770 B2 1/2006 Hood .............................. 606/41
6,991,631 B2 1/2006 Woloszko et al. .............. 606/41
7,001,382 B2 2/2006 Gallo .............................. 606/41
7,004,941 B2 2/2006 Tvinnereim et al. ............ 606/41
7,010,353 B2 3/2006 Gan et al. ........................ 607/50
7,041,102 B2 5/2006 Truckai et al. .................. 606/51
7,070,596 B1 7/2006 Woloszko et al. .............. 606/41
7,090,672 B2 8/2006 Underwood et al. ........... 606/41
7,094,215 B2 8/2006 Davison et al. ................. 604/22
7,094,231 B1 8/2006 Ellman et al. ................... 606/37
7,104,986 B2 9/2006 Hovda et al. .................... 606/32
7,115,139 B2 10/2006 McClurken et al. ............ 607/96
7,131,969 B1 11/2006 Hovda et al. .................... 606/45
7,169,143 B2 1/2007 Eggers et al. ................... 606/32
7,179,255 B2 2/2007 Lettice et al. ................... 606/32
7,186,234 B2 3/2007 Dahla et al. ..................... 604/22
7,192,428 B2 3/2007 Eggers et al. ................... 606/41
7,201,750 B1 4/2007 Eggers et al. ................... 606/41
7,217,268 B2 5/2007 Eggers et al. ................... 606/32
7,223,265 B2 5/2007 Keppel ............................ 606/41
7,241,293 B2 7/2007 Davison ........................ 600/410
7,247,155 B2 7/2007 Hoey et al. ...................... 606/34
7,270,658 B2 9/2007 Woloszko et al. .............. 606/32
7,270,659 B2 9/2007 Ricart et al. .................... 606/32
7,270,661 B2 9/2007 Dahla et al. ..................... 606/41
7,271,363 B2 9/2007 Lee et al. ................. 219/121.43
7,276,061 B2 10/2007 Schaer et al. ................... 607/41
7,276,063 B2 10/2007 Davison et al. ................. 606/45
7,278,994 B2 10/2007 Goble ............................. 606/41
7,282,048 B2 10/2007 Goble et al. .................... 606/34
7,297,143 B2 11/2007 Woloszko et al. .............. 606/41
7,297,145 B2 11/2007 Woloszko et al. .............. 606/41
7,318,823 B2 1/2008 Sharps et al. ................... 606/32
7,331,956 B2 2/2008 Hovda et al. .................... 606/32
7,335,199 B2 2/2008 Goble et al. .................... 606/41
RE40,156 E 3/2008 Sharps et al. ................... 606/32
7,344,532 B2 3/2008 Goble et al. .................... 606/34
7,357,798 B2 4/2008 Sharps et al. ................... 606/32
7,387,625 B2 6/2008 Hovda et al. .................... 606/32
7,419,488 B2 9/2008 Ciarrocca et al. ............... 606/41
7,429,260 B2 9/2008 Underwood et al. ........... 606/32
7,429,262 B2 9/2008 Woloszko et al. .............. 606/46
7,435,247 B2 10/2008 Woloszko et al. .............. 604/45
7,442,191 B2 10/2008 Hovda et al. .................... 606/41
7,445,618 B2 11/2008 Eggers et al. ................... 604/48
7,449,021 B2 11/2008 Underwood et al. ........... 606/32
7,462,178 B2 12/2008 Woloszko et al. ............ 607/105
7,468,059 B2 12/2008 Eggers et al. ................... 606/32
7,491,200 B2 2/2009 Underwood et al. ........... 606/32
7,507,236 B2 3/2009 Eggers et al. ................... 606/41
7,527,624 B2 5/2009 Dubnack et al. ................ 606/41
7,572,251 B1 8/2009 Davison et al. ............... 604/500
7,632,267 B2 12/2009 Dahla ............................. 606/41
7,678,069 B1 3/2010 Baker et al. ..................... 604/22
7,691,101 B2 4/2010 Davison et al. ................. 606/41
7,699,830 B2 4/2010 Martin .......................... 604/540
7,704,249 B2 4/2010 Woloszko et al. .............. 606/48
7,708,733 B2 5/2010 Sanders et al. .................. 606/41
7,722,601 B2 5/2010 Wham et al. .................... 606/34
7,785,322 B2 * 8/2010 Penny et al. .................... 606/34
7,824,398 B2 11/2010 Woloszko et al. .............. 606/45
7,862,560 B2 1/2011 Marion ........................... 606/34
7,879,034 B2 2/2011 Woloszko et al. .............. 606/48
7,892,230 B2 2/2011 Woloszko et al. .............. 606/41
7,901,403 B2 3/2011 Woloszko et al. .............. 606/48
7,985,072 B2 7/2011 Belikov et al. ................ 433/215
7,988,689 B2 8/2011 Woloszko et al. .............. 606/41
8,012,153 B2 9/2011 Woloszko et al. .............. 606/48
8,114,071 B2 2/2012 Woloszko et al. .............. 606/32
D658,760 S 5/2012 Cox et al. ..................... D24/144
8,192,424 B2 6/2012 Woloszko ....................... 606/40
8,303,583 B2 11/2012 Hosier et al. .................... 606/48
8,568,405 B2 10/2013 Cox et al. ........................ 606/41
8,574,187 B2 11/2013 Marion ........................... 606/37
2002/0029036 A1 3/2002 Goble et al. .................... 606/38
2002/0042612 A1 4/2002 Hood et al. ..................... 606/50
2002/0151882 A1 10/2002 Marko et al. .................... 606/28
2002/0183739 A1 12/2002 Long .............................. 606/41
2003/0013986 A1 1/2003 Saadat ......................... 600/549
2003/0014045 A1 1/2003 Russell ........................... 606/41
2003/0014047 A1 1/2003 Woloszko et al. .............. 606/41
2003/0088245 A1 5/2003 Woloszko et al. .............. 606/41
2003/0158545 A1 8/2003 Hovda et al. .................... 606/32
2003/0171743 A1 9/2003 Tasto et al. ...................... 606/32
2003/0181903 A1 9/2003 Hood et al. ..................... 606/49
2003/0208196 A1 11/2003 Stone ............................. 606/41
2003/0212396 A1 11/2003 Eggers et al. ................... 606/41
2003/0216725 A1 11/2003 Woloszko et al. .............. 606/41
2003/0216732 A1 11/2003 Truckai et al. .................. 606/49
2003/0232048 A1 12/2003 Yang et al. ................. 424/141.1
2004/0030330 A1 2/2004 Brassell et al. ................. 606/41
2004/0116922 A1 6/2004 Hovda et al. .................... 606/41

(56) References Cited

U.S. PATENT DOCUMENTS

| | | | | |
|---|---|---|---|---|
| 2004/0127893 | A1 | 7/2004 | Hovda | 606/41 |
| 2004/0186418 | A1 | 9/2004 | Karashima | 604/20 |
| 2004/0215183 | A1* | 10/2004 | Hoey et al. | 606/34 |
| 2004/0230190 | A1 | 11/2004 | Dahla et al. | 604/41 |
| 2005/0004634 | A1 | 1/2005 | Ricart et al. | 606/41 |
| 2005/0033278 | A1 | 2/2005 | McClurken et al. | 606/34 |
| 2005/0245923 | A1 | 11/2005 | Christopherson et al. | 606/41 |
| 2005/0261754 | A1 | 11/2005 | Woloszko et al. | 606/32 |
| 2005/0273091 | A1 | 12/2005 | Booth et al. | 607/99 |
| 2006/0036237 | A1 | 2/2006 | Davison et al. | 606/41 |
| 2006/0095031 | A1 | 5/2006 | Ormsby | 606/34 |
| 2006/0161148 | A1 | 7/2006 | Behnke | 606/34 |
| 2006/0189971 | A1 | 8/2006 | Tasto et al. | 606/32 |
| 2006/0253117 | A1 | 11/2006 | Hovda et al. | 128/898 |
| 2006/0259025 | A1 | 11/2006 | Dahla | 607/108 |
| 2007/0106288 | A1 | 5/2007 | Woloszko et al. | 606/41 |
| 2007/0149966 | A1 | 6/2007 | Dahla et al. | 606/41 |
| 2007/0161981 | A1 | 7/2007 | Sanders et al. | 606/41 |
| 2007/0179495 | A1 | 8/2007 | Mitchell et al. | 606/41 |
| 2008/0077128 | A1 | 3/2008 | Woloszko et al. | 606/41 |
| 2008/0138761 | A1 | 6/2008 | Pond | 433/29 |
| 2008/0140069 | A1 | 6/2008 | Filloux et al. | 606/41 |
| 2008/0154255 | A1 | 6/2008 | Panos et al. | 606/33 |
| 2008/0167645 | A1 | 7/2008 | Woloszko | 606/40 |
| 2008/0243116 | A1 | 10/2008 | Anderson | 606/41 |
| 2008/0300590 | A1 | 12/2008 | Horne et al. | 606/35 |
| 2009/0209956 | A1 | 8/2009 | Marion | 606/34 |
| 2009/0222001 | A1 | 9/2009 | Greeley | 606/33 |
| 2010/0121317 | A1 | 5/2010 | Lorang et al. | 606/41 |
| 2010/0152726 | A1 | 6/2010 | Cadouri et al. | 606/41 |
| 2010/0228246 | A1 | 9/2010 | Marion | 606/37 |
| 2010/0292689 | A1 | 11/2010 | Davison et al. | 606/41 |
| 2010/0318083 | A1 | 12/2010 | Davison et al. | 606/41 |
| 2010/0324549 | A1 | 12/2010 | Marion | 606/37 |
| 2011/0137308 | A1 | 6/2011 | Woloszko et al. | 606/41 |
| 2011/0208177 | A1 | 8/2011 | Brannan | 606/33 |
| 2011/0245826 | A1 | 10/2011 | Woloszko et al. | 606/41 |
| 2012/0083782 | A1 | 4/2012 | Stalder et al. | 606/41 |
| 2012/0095453 | A1 | 4/2012 | Cox et al. | 606/33 |
| 2012/0095454 | A1 | 4/2012 | Cox et al. | 606/33 |
| 2012/0109123 | A1 | 5/2012 | Woloszko et al. | 606/45 |
| 2012/0196251 | A1 | 8/2012 | Taft et al. | 433/216 |
| 2012/0197344 | A1 | 8/2012 | Taft et al. | 607/51 |
| 2013/0116680 | A1 | 5/2013 | Woloszko | 606/33 |
| 2014/0018798 | A1 | 1/2014 | Cox et al. | 606/41 |
| 2014/0025065 | A1 | 1/2014 | Marion | 606/33 |

FOREIGN PATENT DOCUMENTS

| | | | | |
|---|---|---|---|---|
| DE | 69635311 | T2 | 4/2007 | A61B 18/12 |
| EP | 423757 | | 3/1996 | A61B 17/39 |
| EP | 0703461 | A2 | 3/1996 | G01B 27/02 |
| EP | 0740926 | A2 | 11/1996 | A61B 17/39 |
| EP | 0754437 | A2 | 1/1997 | A61B 17/39 |
| EP | 0694290 | B1 | 11/2000 | A61B 18/04 |
| EP | 1334699 | | 8/2003 | A61B 18/12 |
| EP | 1428480 | | 6/2004 | A61B 18/12 |
| EP | 1707147 | | 10/2006 | A61B 18/12 |
| FR | 2313949 | | 1/1977 | A61N 3/02 |
| GB | 467502 | | 6/1937 | A61N 1/40 |
| GB | 2160102 | | 12/1985 | A61B 17/38 |
| GB | 2299216 | | 9/1996 | H01F 30/12 |
| GB | 2 308 979 | | 7/1997 | A61B 17/36 |
| GB | 2 308 980 | | 7/1997 | A61B 17/36 |
| GB | 2 308 981 | | 7/1997 | A61B 17/36 |
| GB | 2 327 350 | | 1/1999 | A61B 17/39 |
| GB | 2 327 351 | | 1/1999 | A61B 17/39 |
| GB | 2 327 352 | | 1/1999 | A61B 17/39 |
| GB | 2333455 | | 7/1999 | G01K 11/12 |
| GB | 2406793 | | 4/2005 | A61B 18/00 |
| JP | 57-57802 | | 4/1982 | A61B 1/00 |
| JP | 57-117843 | | 7/1982 | A61B 17/39 |
| WO | 90/03152 | | 4/1990 | A61B 17/39 |
| WO | 90/07303 | | 7/1990 | A61B 17/39 |
| WO | 92/21278 | | 12/1992 | A61B 5/04 |
| WO | 93/13816 | | 7/1993 | A61B 17/36 |
| WO | 93/20747 | | 10/1993 | A61B 5/00 |
| WO | 94/04220 | | 3/1994 | A61N 1/06 |
| WO | 94/08654 | | 4/1994 | A61M 37/00 |
| WO | 94/10921 | | 5/1994 | A61B 18/00 |
| WO | 94/26228 | | 11/1994 | A61B 18/14 |
| WO | 95/34259 | | 12/1995 | A61F 5/48 |
| WO | 96/00040 | | 1/1996 | A61B 18/00 |
| WO | 96/00042 | | 1/1996 | A61B 17/39 |
| WO | 96/39086 | | 12/1996 | A61B 18/12 |
| WO | 97/00646 | | 1/1997 | A61B 17/39 |
| WO | 97/00647 | | 1/1997 | A61B 17/39 |
| WO | 97/18768 | | 5/1997 | A61B 17/39 |
| WO | 97/24073 | | 7/1997 | A61B 17/39 |
| WO | 97/24074 | | 7/1997 | A61B 17/39 |
| WO | 97/24993 | | 7/1997 | A61B 17/39 |
| WO | 97/24994 | | 7/1997 | A61B 17/39 |
| WO | 97/43971 | | 11/1997 | A61B 17/39 |
| WO | 97/48345 | | 12/1997 | A61B 17/39 |
| WO | 97/48346 | | 12/1997 | A61B 17/39 |
| WO | 98/07468 | | 2/1998 | A61N 1/40 |
| WO | 98/26724 | | 6/1998 | A61B 17/36 |
| WO | 98/27879 | | 7/1998 | A61B 17/36 |
| WO | 98/27880 | | 7/1998 | A61B 17/39 |
| WO | 98/56324 | | 12/1998 | A61F 7/12 |
| WO | 99/20213 | | 4/1999 | A61F 7/12 |
| WO | 99/51155 | | 10/1999 | A61B 17/36 |
| WO | 99/51158 | | 10/1999 | A61B 17/39 |
| WO | 99/56648 | | 11/1999 | A61B 17/39 |
| WO | 00/00098 | | 1/2000 | A61B 17/36 |
| WO | 00/09053 | | 2/2000 | A61F 7/12 |
| WO | 01/24720 | | 4/2001 | A61B 18/18 |
| WO | 01/87154 | | 5/2001 | A61B 5/05 |
| WO | 01/95819 | | 12/2001 | A61B 18/14 |
| WO | 02/36028 | | 5/2002 | A61B 18/12 |
| WO | 02/102255 | | 12/2002 | A61B 17/20 |
| WO | 03/024305 | | 3/2003 | |
| WO | 03/092477 | | 11/2003 | |
| WO | 2004/026150 | | 4/2004 | A61B 17/22 |
| WO | 2004/071278 | | 8/2004 | |
| WO | 2005/125287 | | 12/2005 | A61B 18/00 |
| WO | 2007/006000 | | 1/2007 | A61B 18/14 |
| WO | 2007/056729 | | 5/2007 | A61B 18/14 |
| WO | 2010/052717 | | 5/2010 | A61B 18/14 |
| WO | 2012/050636 | | 4/2012 | A61B 18/14 |
| WO | 2012/050637 | | 4/2012 | A61B 18/14 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.

O'Neill et al., "Percutaneous Plasma Discectomy Stimulates Repair in Injured Porcine Intervertebral Discs", Dept. of Orthopaedic Surgery, Dept. of Radiology University of California at San Francisco, CA, 3 pgs.

Rand et al., "Effect of Elecctrocautery on Fresh Human Articular Cartilage", J. Arthro. Surg., vol. 1, pp. 242-246, 1985.

European Examination Report for EP 02773432 4 pgs, Sep. 22, 2009.

European Examination Report for EP 05024974 4 pgs, Dec. 5, 2008.

European Examination Report for EP 04708664 7pgs, Sep. 7, 2009.

European Examination Report for EP 02749601.7 4pgs, Dec. 2, 2009.

European Examination Report 2 for EP 04708664 5pgs, May 3, 2010.

European Search Report for EP 02773432 3pgs, Dec. 19, 2008.

European Search Report for EP 04708664.0 5pgs, Apr. 6, 2009.

European Search Report for EP 98953859, 2 pgs, Jul. 2, 2001.

Suppl European Search Report for EP 98953859, 3 pgs, Oct. 18, 2001.

Extended European Search Report for EP09152846, 8pgs, Jan. 5, 2010.

European Search Report for EP 99945039.8, 3 pgs, Oct. 1, 2001.

European Search Report for EP 09152850, 2 pgs, Dec. 29, 2009.

PCT International Preliminary Examination Report for PCT/US02/19261, 3pgs, Mar. 25, 2003.

(56) References Cited

OTHER PUBLICATIONS

PCT International Search Report for PCT/US02/19261, 1 pg, Mailed Sep. 18, 2002.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT International Search Report for PCT/US98/22323, 1 pg, Mailed Mar. 3, 1999.
PCT International Search Report for PCT/US99/14685, 1 pg, Mailed Oct. 21, 1999.
PCT International Search Report for PCT/US99/18289, 1 pg, Mailed Dec. 7, 1999.
PCT Notification of International Preliminary Examination Report for PCT/US98/22323, 5 pgs, Mailed Nov. 28, 2000.
PCT Notification of International Preliminary Examination Report for PCT/US99/14685, 4 pgs, Mailed Feb. 20, 2001.
PCT Notification of International Preliminary Examination Report for PCT/US99/18289, 4 pgs, Mailed Jul. 7, 2000.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
PCT Written Opinion of the International Searching Authority for PCT/US04/03614, 4 pgs, Mailed Sep. 14, 2004.
PCT Notification of the International Search Report and Written Opinion for PCT/US2011/033784 11 pgs, Mailed Jul. 18, 2011.
PCT Notification of the International Search Report and Written Opinion for PCT/US2011/033761 11 pgs, Mailed Jul. 22, 2011.
UK Search Report for GB0800129.9 2pgs, May 8, 2008.
UK Search Report for GB0805062.7 1 pg, Jul. 16, 2008.
UK Search Report for GB0900604.0 4 pgs, May 15, 2009.
UK Search Report for GB1110342.1 3pgs, Oct. 18, 2011.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, in Vitro Tissue Ablation Studies and in Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2_{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55_{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.

(56) References Cited

OTHER PUBLICATIONS

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: a Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and Streptococcus Mutans", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for in Vivo Medical Treatment: Recent Developments and Perspectives", Plasma Sources Sci. Technol. 15, pp. S169-S180, Oct. 6, 2006.
Swain, C.P., et al., "Which Electrode, a Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
UK Suppl Search Report for GB1110342.1 2pgs, Aug. 16, 2012.

* cited by examiner

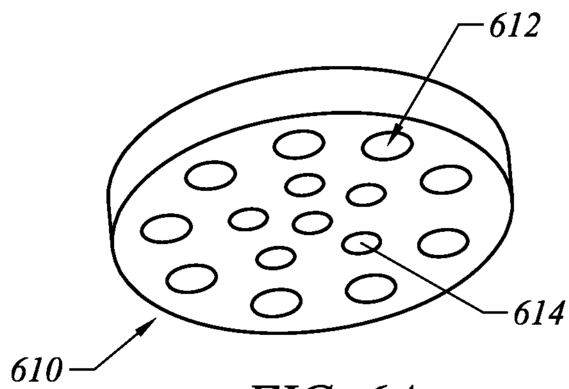
FIG. 6A
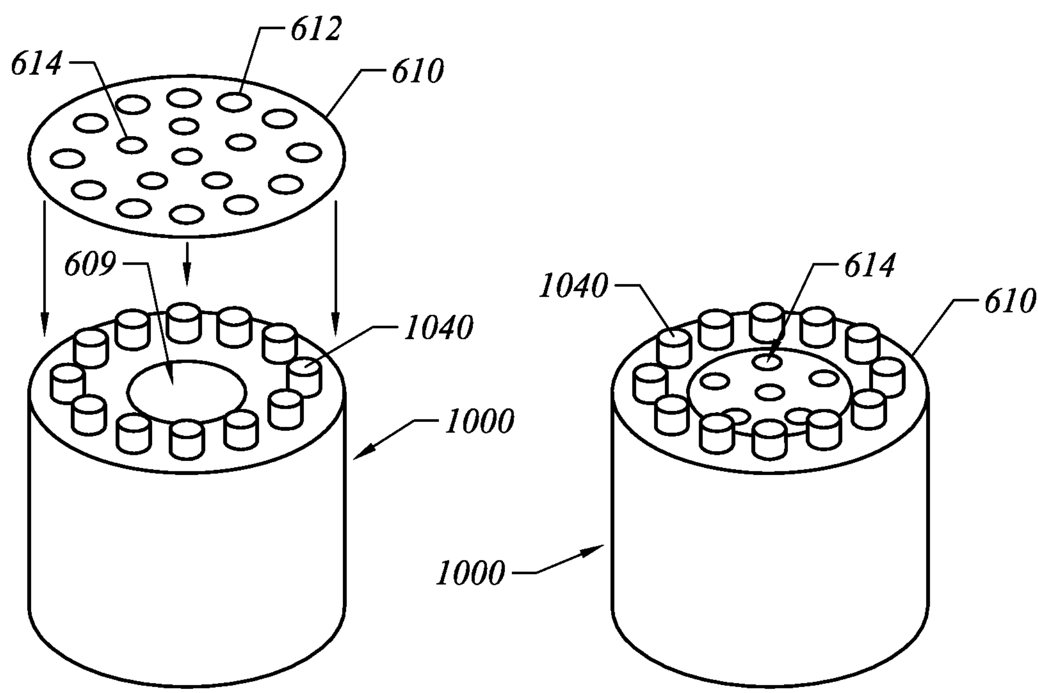
FIG. 6B
FIG. 6C

ELECTROSURGICAL SYSTEM WITH SUCTION CONTROL APPARATUS, SYSTEM AND METHOD

CROSS-REFERENCE TO RELATED APPLICATIONS

This application is a divisional of U.S. application Ser. No. 11/969,283 filed Jan. 4, 2008, now U.S. Pat. No. 8,192,424, which claims the benefit of U.S. Provisional Application No. 60/883,698, filed Jan. 5, 2007, both of which are incorporated herein by reference.

TECHNICAL FIELD OF THE INVENTION

The present invention relates generally to the field of electrosurgery and, more particularly, to surgical devices and methods which employ high frequency voltage to cut and ablate tissue and utilize suction to remove the ablated tissue.

BACKGROUND

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Current electrosurgical device and procedures, however, suffer from a number of disadvantages. For example, monopolar devices generally direct electric current along a defined path from the exposed or active electrode through the patient's body to the return electrode, which is externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying tissue along and surrounding this pathway.

Bipolar electrosurgical devices have an inherent advantage over monopolar devices because the return current path does not flow through the patient. In bipolar electrosurgical devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

The use of electrosurgical procedures (both monopolar and bipolar) in electrically conductive environments can be further problematic. For example, many arthroscopic procedures require flushing of the region to be treated with isotonic saline (also referred to as normal saline), both to maintain an isotonic environment and to keep the field of viewing clear. The presence of saline, which is a highly conductive electrolyte, can also cause shorting of the electrosurgical electrode in both monopolar and bipolar modes. Such shorting causes unnecessary heating in the treatment environment and can further cause non-specific tissue destruction.

Many surgical procedures, such as oral, laparoscopic and open surgical procedures, are not performed with the target tissue submerged under an irrigant. In laparoscopic procedures, such as the resection of the gall bladder from the liver, for example, the abdominal cavity is pressurized with carbon dioxide (pneumoperitoneum) to provide working space for the instruments and to improve the surgeon's visibility of the surgical site. Other procedures, such as the ablation of muscle or gingiva tissue in the mouth, the ablation and necrosis of diseased tissue, or the ablation of epidermal tissue, are also typically performed in a "dry" environment or field (i.e., not submerged under an electrically conducting irrigant).

Present electrosurgical techniques used for tissue ablation also suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 μm, frequently greater than 800 μm, and sometimes as great as 1700 μm. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

In an effort to overcome at least some of these limitations of electrosurgery, laser apparatus have been developed for use in arthroscopic and other procedures. Lasers do not suffer from electrical shorting in conductive environments, and certain types of lasers allow for very controlled cutting with limited depth of necrosis. Despite these advantages, laser devices suffer from their own set of deficiencies. In the first place, laser equipment can be very expensive because of the costs associated with the laser light sources. Moreover, those lasers which permit acceptable depths of necrosis (such as eximer lasers, erbium:YAG lasers, and the like) provide a very low volumetric ablation rate, which is a particular disadvantage in cutting and ablation of fibrocartilage, articular cartilage, and meniscal tissue. The holmium:YAG and Nd:YAG lasers provide much higher volumetric ablation rates, but are much less able to control depth of necrosis than are the slower laser devices. The CO2 lasers provide high rate of ablation and low depth of tissue necrosis, but cannot operate in a liquid-filled cavity.

For these and other reasons, improved systems and methods are desired for the electrosurgical ablation and cutting of tissue. These systems and methods should be capable of selectively cutting and ablating tissue and other body structures in electrically conductive environments, such as regions filled with blood or irrigated with electrically conductive solutions, such as isotonic saline, and in relatively dry environments, such as those encountered in oral, dermatological, laparoscopic, thoracosopic and open surgical procedures. Such apparatus and methods should be able to perform cutting and ablation of tissues, while limiting the depth of necrosis and limiting the damage to tissue adjacent to the treatment site.

The assignee of the present invention developed Coblation® technology. Coblation® technology involves the application of a high frequency voltage difference between one or more active electrode(s) and one or more return electrode(s) to develop high electric field intensities in the vicinity of the target tissue in order to treat said tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

The electrosurgical devices described above may incorporate a suction lumen to carry away blood, tissue or other material from the treatment site. Presently available devices that utilize suction typically access vacuum pressure from a surgical vacuum source that is self-regulated to maintain a pre-set vacuum pressure. One problem associated with such systems is that the flow of liquid, gas and/or tissue particles in the vicinity of the treatment end of device may negatively affect the efficacy of such electrosurgical devices.

SUMMARY OF THE INVENTION

The present invention provides a system and method for selectively applying electrical energy to structures within or on the surface of a patient's body and controlling flow through an associated suction apparatus to remove the ablated tissue. The system and method allow the surgical team to perform electrosurgical interventions, such as ablation and cutting of body structures, while controlling the suction flow rate according to certain operating parameters in order to provide or maintain a desired operating condition of the electrosurgical device. The system and method of the present invention are useful for surgical procedures in relatively dry environments, such as treating and shaping gingiva, for tissue dissection, e.g., separation of gall bladder from the liver, ablation and necrosis of diseased tissue, such as fibroid tumors, and dermatological procedures involving surface tissue ablation on the epidermis, such as scar or tattoo removal, tissue rejuvenation and the like. The present invention may also be useful in electrically conducting environments, such as arthroscopic or cystoscopic surgical procedures. In addition, the present invention is useful for canalizing or boring channels or holes through tissue, such as the ventricular wall of the heart during transmyocardial revascularization procedures.

The methods of the present invention may include positioning an electrosurgical probe adjacent the target tissue so that at least one active electrode is brought into close proximity to the target site. A return electrode is positioned within an electrically conducting liquid, such as isotonic saline, to generate a current flow path between the target site and the return electrode. High frequency voltage is then applied between the active and return electrode through the current flow path created by the electrically conducting liquid in either a bipolar or monopolar manner. One or more operating parameters of the electrical probe or voltage generator are preferably monitored and used to control the operation of an associated suction apparatus. The probe may then be translated, reciprocated or otherwise manipulated to cut the tissue or effect the desired depth of ablation.

A further understanding of the nature and advantages of the invention will become apparent by reference to the remaining portions of the specification and drawings.

BRIEF DESCRIPTION OF THE DRAWINGS

FIG. 6A-6C illustrate the design of a probe include an screen-type active electrode;

DETAILED DESCRIPTION

Figure 1:
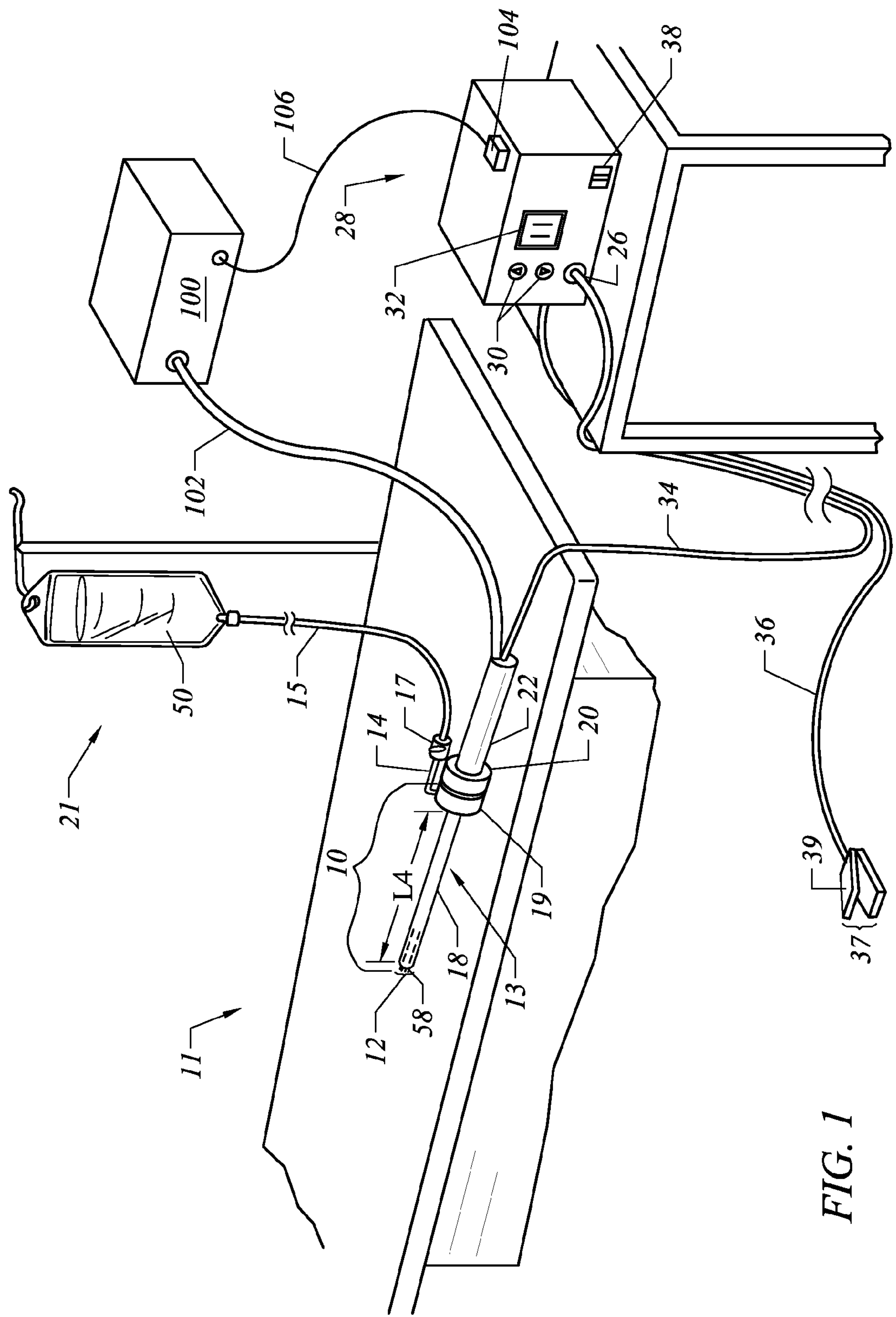
FIG. 1 is a perspective view of the electrosurgical system including an electrosurgical probe, an electrically conducting liquid supply, a suction apparatus and an electrosurgical power supply constructed in accordance with the principles of the present invention.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The systems of the present invention may be configured to address any application wherein a suction system may be utilized in conjunction with an electrosurgical device for treating tissue. The treatment device of the present invention may have a variety of configurations as described above. However, one variation of the invention employs a treatment device using Coblation® technology.

As stated above, the assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882, the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in commonly assigned U.S. Pat. Nos. 6,355,032; 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

A more detailed discussion of applications and devices using Coblation® technology may be found in, for example, U.S. Pat. Nos. 5,697,882; 6,190,381; 6,282,961; 6,296,638; 6,482,201; 6,589,239; 6,746,447; 6,929,640; 6,949,096 and 6,991,631, and U.S. patent application Ser. No. 10/713,643, each of which is incorporated herein by reference.

In one example of a Coblation® device for use with the present embodiments, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use in the present embodiments may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. A single active electrode (or one of a multiple electrodes) may include a screen or mesh type electrode with multiple apertures sized to permit fluid to flow therethrough. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source or generator of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In certain embodiments, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

In certain embodiments of the present system, a suction lumen may be provided with the electrosurgical device. The suction lumen is preferably in communication with a suction source such as a suction pump, and is also in communication with a suction opening positioned proximate to the treatment surface of the electrosurgical device. A portion of the suction lumen may be located internally within the electrosurgical device or may be attached to the exterior of the electrosurgical device. The suction lumen preferably has a diameter sized to effectively remove ablated tissue and other material away from the treatment site. A fluid supply lumen may also be provided. The fluid supply lumen may utilized separate from the electrosurgical device or may be integrated with the electrosurgical device (either on the exterior or within the interior of said device.)

The suction source may encompass any suitable fluid transport apparatus. In some embodiments the suction source may be a suction pump. The suction source may be a positive displacement pump such as, for example, a peristaltic pump. In some embodiments the suction source may comprise a vacuum pump and canister assembly such as may be provided via a wall outlet in a surgical suite.

Certain embodiments of the present disclosure may include a controller device used to periodically receive data related to one or more operating parameters associated with the electrosurgical device or voltage generator, and, responsive to the operating parameter data, send control signals to an associated suction source. The control signals may operate to activate the suction source in conjunction with the use of the electrosurgical device. In other embodiments, the control signals may be used to dynamically adjust fluid flow through the suction source, initiate fluid flow through the suction source, delay initiating fluid flow through the suction source, cease fluid flow through the suction source, decrease fluid flow through the suction source, incrementally increase or decrease fluid flow through the vacuum source, and/or maintain a particular fluid flow through the suction source if the operating parameters remain within a pre-selected value range. In other embodiments, the control signals from the controller device may dynamically control the pressure at the suction source.

The input signals into the controller may preferably include any input signals indicative of operating conditions at the distal end of the electrosurgical device. These may include, but are not limited to, operating parameters measured by a sensor within an electrosurgical probe, within a generator or within the suction lumen. Such operating parameters my include, buy are not limited to, impedance, electric current (including whether a treatment current has been initiated or stopper), peak electric current and mean electric current for a selected period, peak electric current and RMS voltage for a selected period. For devices that may operate in more than one operating mode, such as an ablation mode and a coagulation mode, the operating parameter may be associated with signals indicating the operating mode of the device.

The embodiments of the present device provide a system and method for selectively applying electrical energy to a target location within or on a patient's body and removing tissue and other material from the target location through a fluid transport lumen. In certain embodiments, the flow rate of tissue and associated fluids removed through the transport lumen may be controlled according to operating parameters associated with an electrosurgical probe or a voltage generator. The system and method may be utilized for the treatment of solid tissue or the like, particularly including gingival tissues and mucosal tissues located in the mouth or epidermal tissue on the outer skin. In addition, tissues which may be treated by the system and method of the present invention include tumors, abnormal tissues, and the like. The embodiments described herein may also be used for canalizing or boring channels or holes through tissue, such as the ventricular wall during transmyocardial revascularization procedures. It will be appreciated that the system and method can be applied equally well to procedures involving other tissues of the body, as well as to other procedures including open surgery, laparoscopic surgery, thoracoscopic surgery, and other endoscopic surgical procedures. Notably, the system and method described herein is particularly useful in procedures where the tissue site is flooded or submerged with an electrically conducting fluid, such as isotonic saline, e.g., arthroscopic surgery and the like.

In one embodiment, a single active electrode or an electrode array distributed over a distal contact surface of a probe may be used. The electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, and the like. The electrode terminals may be independently current-limited by using isolating the terminals from each other and connecting each terminal to a separate power source that is isolated from the other electrode terminals. Alternatively, the electrode terminals may be connected to each other at either the proximal or distal ends of the probe to form a single wire that couples to a power source.

The electrosurgical probe may comprise a shaft having a proximal end and a distal end which supports an active electrode. The shaft may assume a wide variety of configurations, with the primary purpose being to mechanically support the active electrode and permit the treating physician to manipulate the electrode from a proximal end of the shaft. Usually, the shaft will be a narrow-diameter rod or tube, more usually having dimensions which permit it to be introduced into a body cavity, such as the mouth or the abdominal cavity, through an associated trocar or cannula in a minimally invasive procedure, such as arthroscopic, laparoscopic, thoracoscopic, and other endoscopic procedures. Thus, the shaft will typically have a length of at least 5 cm for oral procedures and at least 10 cm, more typically being 20 cm, or longer for endoscopic procedures. The shaft will typically have a diameter of at least 1 mm and frequently in the range from 1 to 10 mm. Of course, for dermatological procedures on the outer skin, the shaft may have any suitable length and diameter that would facilitate handling by the surgeon.

The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Specific shaft designs will be described in detail in connection with the figures hereinafter.

The circumscribed area of the electrode array may be in the range from 0.25 mm2 to 75 mm2, preferably from 0.5 mm2 to 40 mm2, and will usually include at least two isolated electrode terminals, more usually at least four electrode terminals, preferably at least six electrode terminals, and often 50 or more electrode terminals, disposed over the distal contact surfaces on the shaft. By bringing the electrode array(s) on the contact surface(s) in close proximity with the target tissue and applying high frequency voltage between the array(s) and an additional common or return electrode in direct or indirect contact with the patient's body, the target tissue is selectively ablated or cut, permitting selective removal of portions of the target tissue while desirably minimizing the depth of necrosis to surrounding tissue. In particular, this invention provides a method and apparatus for effectively ablating and cutting tissue which may be located in close proximity to other critical organs, vessels or structures (e.g., teeth, bone) by simultaneously (1) causing electrically conducting liquid to flow between the common and active electrodes, (2) applying electrical energy to the target tissue surrounding and immediately adjacent to the tip of the probe, (3) bringing the active electrode(s) in close proximity with the target tissue using the probe itself, (4) controlling the fluid flow through or pressure within an associated suction source and (5) optionally moving the electrode array axially and/or transversely over the tissue.

Electrosurgical probes according to the present invention may include a single active electrode or two or more active electrodes. In some embodiments the active electrodes may be formed around a suction opening. Other embodiments may include a screen electrode with multiple apertures formed therein to allow fluid to flow therethrough. One embodiment includes at least one ring-shaped electrode with an opening formed therein through with a suction opening may be provided. The active electrode or electrodes may be provided in any suitable number and configuration (including placement with respect to the suction lumen opening) for treating tissue.

The tip region of the probe may be composed of many independent electrode terminals designed to deliver electrical energy in the vicinity of the tip. The selective application of electrical energy to the target tissue is achieved by connecting each individual electrode terminal and the common electrode to a power source having independently controlled or current limited channels. The common electrode may be a tubular member of conductive material proximal to the electrode array at the tip which also serves as a conduit for the supply of the electrically conducting liquid between the active and common electrodes. The application of high frequency voltage between the common electrode and the electrode array results in the generation of high electric field intensities at the distal tips of the electrodes with conduction of high frequency current from each individual electrode terminal to the common electrode. The current flow from each individual electrode terminal to the common electrode is controlled by either active or passive means, or a combination thereof, to deliver electrical energy to the target tissue while minimizing energy delivery to surrounding (non-target) tissue and any conductive fluids which may be present (e.g., blood, electrolytic irrigants such as saline, and the like).

In a preferred aspect, this invention takes advantage of the differences in electrical resistivity between the target tissue (e.g., gingiva, muscle, fascia, tumor, epidermal, heart or other tissue) and the surrounding conductive liquid (e.g., isotonic saline irrigant). By way of example, for any selected level of applied voltage, if the electrical conduction path between the common electrode and one of the individual electrode terminals within the electrode array is isotonic saline irrigant liquid (having a relatively low electrical impedance), the current control means connected to the individual electrode will limit current flow so that the heating of intervening conductive liquid is minimized. On the other hand, if a portion of or all of the electrical conduction path between the common electrode and one of the individual electrode terminals within the electrode array is gingival tissue (having a relatively higher electrical impedance), the current control circuitry or switch connected to the individual electrode will allow current flow sufficient for the deposition of electrical energy and associated ablation or electrical breakdown of the target tissue in the immediate vicinity of the electrode surface.

The application of a high frequency voltage between the common or return electrode and the electrode array for appropriate time intervals effects ablation, cutting or reshaping of the target tissue. The tissue volume over which energy is dissipated (i.e., a high voltage gradient exists) may be precisely controlled, for example, by the use of a multiplicity of small electrodes whose effective diameters range from about 2 mm to 0.01 mm, preferably from about 1 mm to 0.05 mm, and more preferably from about 0.5 mm to 0.1 mm. Electrode areas for both circular and non-circular terminals will have a contact area (per electrode) below 5 mm2, preferably being in the range from 0.0001 mm2 to 1 mm2, and more preferably from 0.005 mm2 to 0.5 mm2. The use of small diameter electrode terminals increases the electric field intensity and reduces the extent or depth of tissue necrosis as a consequence of the divergence of current flux lines which emanate from the exposed surface of each electrode terminal. Energy deposition in tissue sufficient for irreversible damage (i.e., necrosis) has been found to be limited to a distance of about one-half to one electrode diameter. This is a particular advantage over prior electrosurgical probes employing single and/or larger electrodes where the depth of tissue necrosis may not be sufficiently limited.

In some embodiments a high frequency voltage may be applied between the active electrode surface and the return electrode to develop high electric field intensities in the vicinity of the target tissue site. The high electric field intensities lead to electric field induced molecular breakdown of target tissue through molecular dissociation (rather than thermal evaporation or carbonization). In other words, the tissue structure is volumetrically removed through molecular disintegration of complex organic molecules into non-viable atoms and molecules, such as hydrogen, oxides of carbon, hydrocarbons and nitrogen compounds. This molecular disintegration completely removes the tissue structure, as opposed to transforming the tissue material from a solid form directly to a vapor form, as is typically the case with ablation.

The high electric field intensities may be generated by applying a high frequency voltage that is sufficient to vaporize the electrically conducting liquid over at least a portion of the active electrode(s) in the region between the distal tip of the active electrode and the target tissue. Since the vapor layer or vaporized region has a relatively high electrical impedance, it increases the voltages differential between the active electrode tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof.

The necessary conditions for forming a vapor layer near the active electrode tip(s), ionizing the atom or atoms within the vapor layer and inducing the discharge of energy from plasma within the vapor layer will depend on a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Based on initial experiments, applicants believe that the ionization of atoms within the vapor layer produced in isotonic saline (containing sodium chloride) leads to the generation of energetic photons having wavelengths, by way of example, in the range of 306 to 315 nanometers (ultraviolet spectrum) and 588 to 590 nanometers (visible spectrum). In addition, the free electrons within the ionized vapor layer are accelerated in the high electric fields near the electrode tip(s). When the density of the vapor layer (or within a bubble formed in the electrically conducting liquid) becomes sufficiently low (i.e., less than approximately 1020 atoms/cm3 for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The photon energy produces photoablation through photochemical and/or photothermal processes to disintegrate tissue thicknesses as small as several cell layers of tissue at the target site. This photoablation is a "cold" ablation, which means that the photon energy transfers very little heat to tissue beyond the boundaries of the region of tissue ablated. The cold ablation provided by photon energy can be precisely controlled to only affect a thin layer of cells without heating or otherwise damaging surrounding or underlying cells. The depth of necrosis will be typically be about 0 to 400 microns and usually 10 to 200 microns. Applicants believe that the "fragments" of disintegrated tissue molecules carry away much of the energy which is deposited on the surface of the target tissue, thereby allowing molecular disintegration of tissue to occur while limiting the amount of heat transfer to the surrounding tissue.

In addition, other competing mechanisms may be contributing to the ablation of tissue. For example, tissue destruction or ablation may also be caused by dielectric breakdown of the tissue structural elements or cell membranes from the highly concentrated intense electric fields at the tip portions of the electrode(s). According to the teachings of the present invention, the active electrode(s) are sized and have exposed surfaces areas which, under proper conditions of applied voltage, cause the formation of a vaporized region or layer over at least a portion of the surface of the active electrode(s). This layer or region of vaporized electrically conducting liquid creates the conditions necessary for ionization within the vaporized region or layer and the generation of energetic electrons and photons. In addition, this layer or region of vaporized electrically conducting liquid provides a high electrical impedance between the electrode and the adjacent tissue so that only low levels of current flow across the vaporized layer or region into the tissue, thereby minimizing joulean heating in, and associated necrosis of, the tissue.

As discussed above, applicants have found that the density of the electrically conducting liquid at the distal tips of the active electrodes should be less than a critical value to form a suitable vapor layer. For aqueous solutions, such as water or isotonic saline, this upper density limit is approximately 1020 atoms/cm3, which corresponds to about $3\times10^{-3}$ grams/cm3. Applicant's also believe that once the density in the vapor layer reaches a critical value (e.g., approximately 1020 atoms/cm3 for aqueous solutions), electron avalanche occurs. The growth of this avalanche is retarded when the space charge generated fields are on the order of the external field. Spatial extent of this region should be larger than the distance required for an electron avalanche to become critical and for an ionization front to develop. This ionization front develops and propagates across the vapor layer via a sequence of processes occurring the region ahead of the front, viz, heat by electron injection, lowering of the local liquid density below the critical value and avalanche growth of the charged particle concentration.

Electrons accelerated in the electric field within the vapor layer will apparently become trapped after one or a few scatterings. These injected electrons serve to create or sustain a low density region with a large mean free path to enable subsequently injected electrons to cause impact ionization within these regions of low density. The energy evolved at each recombination is on the order of half of the energy band gap (i.e., 4 to 5 eV). It appears that this energy can be transferred to another electron to generate a highly energetic electron. This second, highly energetic electron may have sufficient energy to bombard a molecule to break its bonds, i.e., dissociate the molecule into free radicals.

The electrically conducting liquid should have a threshold conductivity in order to suitably ionize the vapor layer for the inducement of energetic electrons and photons. The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. The electrical conductivity of the channel trailing the ionization front should be sufficiently high to maintain the energy flow required to heat the liquid at the ionization front and maintain its density below the critical level. In addition, when the electrical conductivity of the liquid is sufficiently high, ionic pre-breakdown current levels (i.e., current levels prior to the initiation of ionization within the vapor layer) are sufficient to also promote the initial growth of bubbles within the electrically conducting liquid (i.e., regions whose density is less than the critical density).

Asperities on the surface of the active electrode(s) may promote localized high current densities which, in turn, promote bubble nucleation at the site of the asperities whose enclosed density (i.e., vapor density) is below the critical density to initiate ionization breakdown within the bubble. Hence, a specific configuration of the present invention creates regions of high current densities on the tips of the electrode(s) (i.e., the surface of the electrode(s) which are to engage and ablate or cut tissue). Regions of high current densities can be achieved via a variety of methods, such as producing sharp edges and corners on the distal tips of the electrodes or vapor blasting, chemically etching or mechanically abrading the distal end faces of the active electrodes to produce surface asperities thereon. Alternatively, the electrode terminals may be specifically designed to increase the edge/surface area ratio of the electrode terminals. For example, the electrode terminal(s) may be hollow tubes having a distal, circumferential edge surrounding an opening. The terminals may be formed in an array as described above or in a series of concentric terminals on the distal end of the probe. High current densities will be generated around the circumferential edges of the electrode terminals to promote nucleate bubble formation.

In some embodiments the active electrode(s) may be formed over a contact surface on the shaft of the electrosurgical probe. The common (return) electrode surface will be recessed relative to the distal end of the probe and may be recessed within the conduit provided for the introduction of electrically conducting liquid to the site of the target tissue and active electrode(s). In the exemplary embodiment, the shaft will be cylindrical over most of its length, with the contact surface being formed at the distal end of the shaft. In the case of endoscopic applications, the contact surface may be recessed since it helps protect and shield the electrode terminals on the surface while they are being introduced, particularly while being introduced through the working channel of a trocar channel or a viewing scope.

The area of the contact surface can vary widely, and the contact surface can assume a variety of geometries, with particular areas in geometries being selected for specific applications. Active electrode contact surfaces can have areas in the range from 0.25 mm2 to 50 mm2, usually being from 1 mm2 to 20 mm2. The geometries can be planar, concave, convex, hemispherical, conical, linear “in-line” array or virtually any other regular or irregular shape. Most commonly, the active electrode(s) will be formed at the distal tip of the electrosurgical probe shaft, frequently being planar, disk-shaped, or hemispherical surfaces for use in reshaping procedures or being linear arrays for use in cutting. In some preferred embodiments the active electrode may be a screen or mesh type electrode. Alternatively or additionally, the active electrode(s) may be formed on lateral surfaces of the electrosurgical probe shaft (e.g., in the manner of a spatula), facilitating access to certain body structures in electrosurgical procedures.

During the surgical procedure, the distal end of the probe or the active electrode(s) will be maintained at a small distance away from the target tissue surface. This small spacing allows for the continual resupply of electrically conducting liquid into the interface between the active electrode(s) and the target tissue surface and removal of ablated tissue and other material through a fluid transport or suction lumen. The continual resupply of the electrically conducting liquid and controlled removal of ablated tissue and other material helps to ensure that the thin vapor layer will remain between active electrode(s) and the tissue surface. Moreover, the condition of the vapor layer at the electrode(s) may be monitored, for example, by measuring impedance or electric current at the treatment interface through sensors located in proximity to the probe. Depending on the status of the vapor layer condition measured, the flow of fluid through the suction lumen may be dynamically adjusted through control of the suction apparatus in order to maintain a stable vapor layer. For example, if the impedance at the treatment interface is detected to be above a preferred operating parameter, the flow of fluid through the suction lumen may be initiated or increased. Conversely, if instability in the vapor layer is detected through measurement of an operating condition associated with electrosurgical probe, the flow of fluid through the fluid transport or suction lumen may be decreased or, in some cases, completely ceased. In addition, dynamic movement of the active electrode(s) over the tissue site allows the electrically conducting liquid to cool the tissue surrounding recently ablated areas to minimize thermal damage to this surrounding tissue. In some embodiments the active electrode(s) will be about 0.02 to 2 mm from the target tissue and preferably about 0.05 to 0.5 mm during the ablation process. One method of maintaining this space is to translate and/or rotate the probe transversely relative to the tissue, i.e., a light brushing motion, to maintain a thin vaporized layer or region between the active electrode and the tissue. Of course, if coagulation of a deeper region of tissue is necessary (e.g., for sealing a bleeding vessel imbedded within the tissue), it may be desirable to press the active electrode against the tissue to effect joulean heating therein.

Referring to the drawings in detail, wherein like numerals indicate like elements, an electrosurgical system 11 is shown constructed according to the principles of the present invention. Electrosurgical system 11 generally comprises an electrosurgical probe 10 connected to a power supply 28 for providing high frequency voltage to a target tissue and a liquid source 21 for supplying electrically conducting fluid 50 to probe 10 via fluid supply conduit 15. Fluid supply conduit may include a valve 17 for controlling fluid flow at the distal end thereof 14 and to wand 10.

In an exemplary embodiment as shown in FIG. 1, electrosurgical probe 10 includes an elongated shaft 13 which may be flexible or rigid, with flexible shafts optionally including support cannulas or other structures (not shown). Probe 10 includes a connector 19 at its proximal end and an array 12 of electrode terminals 58 disposed on the distal tip of shaft 13. As discussed above, the present invention may include a variety of electrode configurations that may be employed with electrosurgical probe 10 (include embodiments with a single electrode such as a screen electrode or a screen electrode). A connecting cable 34 has a handle 22 with a connector 20 which can be removably connected to connector 19 of probe 10. The proximal portion of cable 34 has a connector 26 to couple probe 10 to power supply 28. The electrode terminals 58 are electrically isolated from each other and each of the terminals 58 is connected to an active or passive control network within power supply 28 by means of a plurality of individually insulated conductors 42. Power supply 28 has a selection means 30 to change the applied voltage level. Power supply 28 may also be referred to generally as a “generator” herein. Power supply 28 also includes means for energizing the electrodes 58 of probe 10 through the depression of a pedal 39 in a foot pedal 37 positioned close to the user and is connected to power supply 28 via cable 36. The foot pedal 37 may also include a second pedal (not shown) for remotely adjusting the energy level applied to electrodes 58 or for selecting an alternate operating mode.

Suction lumen 102 is in communication with the electrosurgical probe 10 and with suction pump 100. Suction pump 100 is further in electrical communication with controller 104 via cable 106. Suction pump 100 may encompass any suitable fluid transport apparatus. Suction pump 100 may comprise a positive displacement pump such as, for example, a peristaltic pump. In some embodiments the suction pump 100 may comprise a vacuum pump and canister assembly such as may be provided via a wall outlet in a surgical suite.

As shown in the present embodiment, controller 104 may be associated with power supply 28 and may receive input regarding one or more operating parameters therefrom. It should be appreciated that the location of controller 104 may be altered within the present invention, and may alternatively be located within suction pump 100 or provided as an independent component. Controller 104 may also be disposed directly within probe 10. In certain embodiments, controller 104 may either receive operating parameter input from a suitable sensor or sensors within power supply 28 or probe 10. Controller 104 periodically receives data related to one or more operating parameters associated with electrosurgical probe 10 or power supply 28.

The input received by controller 104 may preferably include any input signals indicative of operating conditions at the distal end of the electrosurgical probe. These may include, but are not limited to, operating parameters measured by a sensor within an electrosurgical probe, within a generator or within the suction lumen. The present embodiment shows the controller 104 receiving operating parameter data from power supply 28. Such operating parameters my include, but are not limited to, impedance, electric current (including whether a treatment current has been initiated or stopper), peak electric current and mean electric current for a selected period, peak electric current and RMS voltage for a selected period. For devices that may operate in more than one operating mode, such as an ablation mode and a coagulation mode, the operating parameter may include the operating mode of the device.

In certain embodiments, the operating parameter input data received by controller 104 may be indicative of operating conditions at the distal end of probe 10. For example, the impedance at the distal end of probe 10 may be an operating parameter that is measured by an electrosurgical probe sensor (not shown) and transmitted to controller 104 for processing. Typically, the impedance at electrode terminals 58 increases when a plasma field is established at that location, whereas the impedance is found to decrease as the plasma field becomes unstable. Therefore, a measurement of impedance may provide operating parameter input data indicative of the plasma field and related vapor layer condition proximate electrode terminals 58.

Additionally, an electrosurgical probe sensor may measure electric current at the distal end of probe 10, either for obtaining a current value or to determine whether a treatment current has been initiated or stopped. Electric current data may similarly be transmitted to controller 104 for processing. Further, peak electric current and mean electric current for a selected period, and peak electric current and RMS voltage for a selected period, may be measured by a sensor associated with either probe 10 or power supply 28, and the measured data input transmitted to controller 104 for processing as operating parameter input data of interest.

In other embodiments, probe 10 may be used with a power supply 28 capable of operating in more than one operating mode, such as an ablation mode and a coagulation mode. In an ablation mode, power supply 28 is adapted to provide a relatively high voltage output, in comparison to operation in a coagulation mode, where power supply 28 may be adapted to provide a relatively lower voltage output. In these embodiments, controller 104 may receive input data indicative of which mode power supply 28 is operating. Specifically, a sensor (not shown) associated with power supply 28 may be provided to measure the voltage output of power supply 28, and then transmit such measurements indicating the operating mode of power supply 28 to controller 104 in the form of input data for processing.

Responsive to the operating parameter input received by controller 104, a processor (not shown) associated with controller 104 preferably generates and sends control signals to suction pump 100. In certain embodiments, these control signals may operate to dynamically adjust fluid flow through suction pump 100, initiate fluid flow through suction pump 100, delay initiating fluid flow through suction pump 100, cease fluid flow through suction pump 100, decrease fluid flow through suction pump 100, incrementally increase or decrease fluid flow through suction pump 100, and/or maintain a particular fluid flow through suction pump 100 if the operating parameters remain within a pre-selected value range. In other embodiments, the control signals from controller 104 may dynamically control the pressure at the suction pump 100.

Controller 104 may receive operating parameter input data indicating the status or operating condition of power supply 28. One such embodiment may consist of controller 104 receiving input data as to whether power supply 28 has been activated. Where power supply 28 has been activated and probe 10 is in use, controller 104 may send signals that activate suction pump 100 in response. Similarly, where power supply 28 has been deactivated and probe 10 is not in use, controller 104 may send signals that deactivate suction pump 100. In a related embodiment, controller 104 may receive operating parameter input indicative of the operating mode of power supply 28. In response, controller 104 may initiate or cease fluid flow through suction pump 100. Specifically, controller 104 may initiate fluid flow through suction pump 100 where power supply 28 is detected to be operating in ablation mode, and cease fluid flow through suction pump 100 where power supply 28 is detected to be operating in coagulation mode.

In certain additional embodiments, controller 104 may process input data relative to conditions at the distal end of probe 10, and specifically indicative of the condition of the plasma field and related vapor layer created proximate electrode terminals 58. Suction pump 100 may be deactivated when power supply 28 is initially activated, and the impedance at the distal end of probe 10 may be monitored and measured such that the data indicative of the operating condition of probe 10 may be processed by controller 104. In some instances, when the impedance is measured to be at a desired level (indicating establishment of a stable plasma field and vapor layer at electrode terminals 58) or is measured to exceed a specified threshold value, controller 104 may send a signal to suction pump 100 directing suction pump 100 to initiate fluid flow. Additional embodiments may consist of controller 104 sending signals to suction pump 100 that direct suction pump 100 to modulate its speed in response to collected operating parameter input. For example, if a decrease in the impedance at the distal end of probe 10 is measured during operation, controller 104 may send a signal to suction pump 100 directing it to decrease speed, thereby reducing fluid flow therethrough and at the treatment site. Conversely, if an increase of the impedance at the distal end of probe 10 is measured during operation, controller 104 may send a signal to suction pump 100 directing it to increase speed, thereby increasing fluid flow therethrough.

Suction lumen 102 is preferably in communication within a suction lumen formed within probe 10 (e.g., fluid transport lumen 57 shown in FIGS. 2A and 2B) and having a suction opening positioned proximate to the treatment surface of the electrosurgical device. In alternate embodiments the suction lumen may attached to the exterior of the electrosurgical device.

Figure 2A:
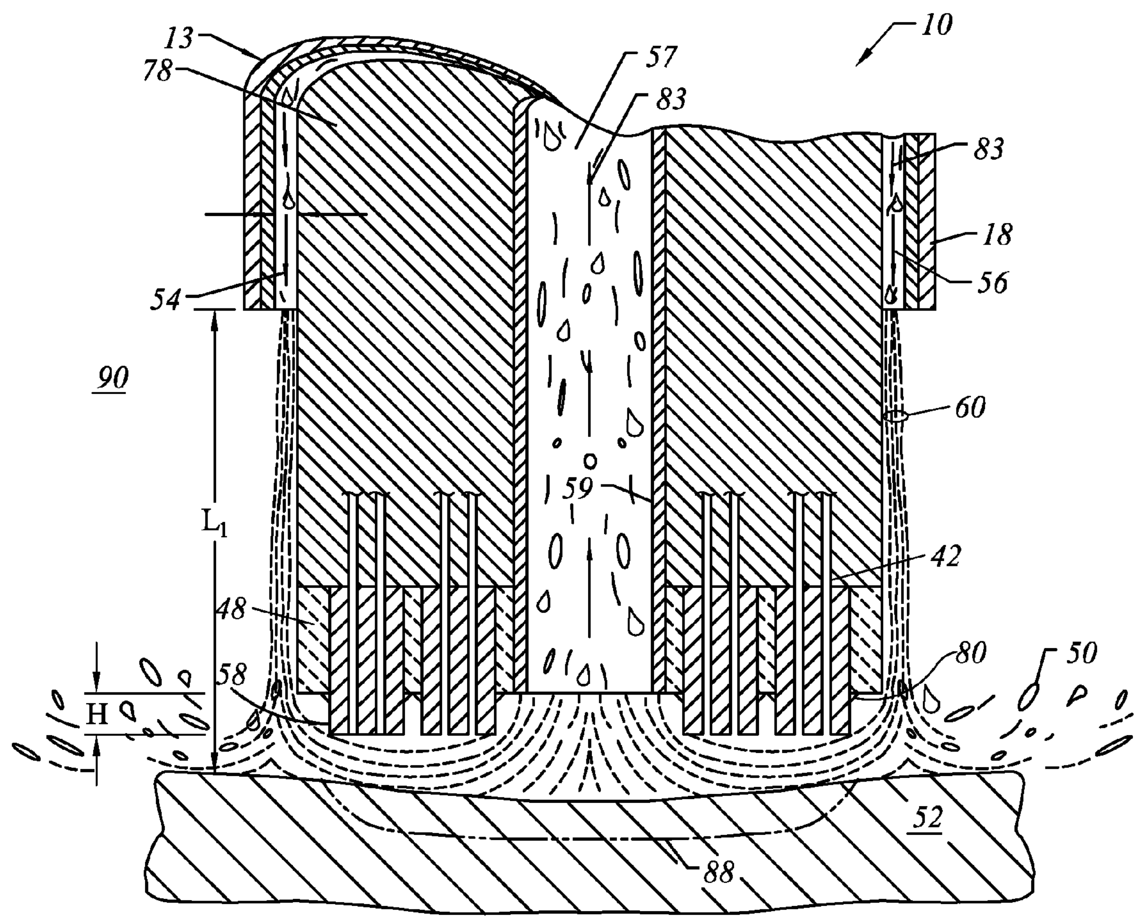
FIGS. 2A and 2B illustrate a probe having a plurality of electrode terminals spaced-apart over an electrode array surface.
Figure 2B:
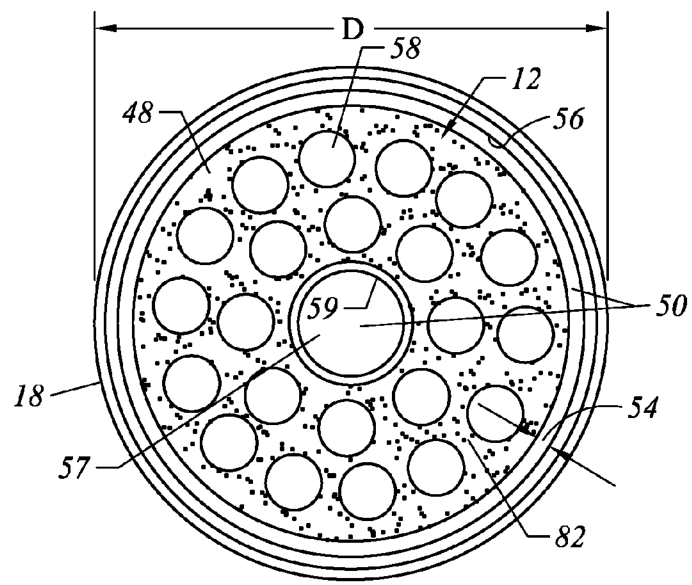
Figure 5:
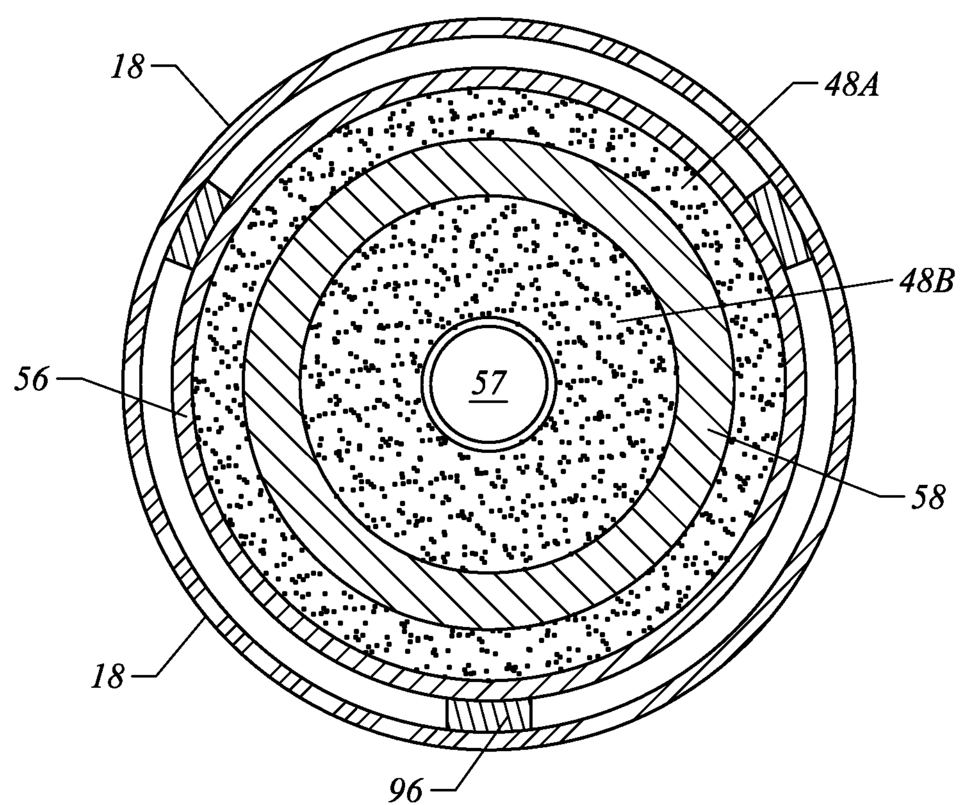
FIG. 5 illustrates the design of a probe include an active electrode with a ring-shaped geometry.

Referring to FIGS. 2A and 2B, the electrically isolated electrode terminals 58 are spaced-apart over an electrode array surface 82. The electrode array surface 82 and individual electrode terminals 58 will usually have dimensions within the ranges set forth above. In the preferred embodiment, the electrode array surface 82 has a circular cross-sectional shape with a diameter D (FIG. 2B) in the range from 0.3 mm to 10 mm. Electrode array surface 82 may also have an oval shape, having a length L in the range of 1 mm to 20 mm and a width W in the range from 0.3 mm to 7 mm, as shown in FIG. 5. The individual electrode terminals 58 will protrude over the electrode array surface 82 by a distance (H) from 0 mm to 2 mm, preferably from 0 mm to 1 mm (see FIG. 3).

It should be noted that the electrode terminals may be flush with the electrode array surface 82, or the terminals may be recessed from the surface. For example, in dermatological procedures, the electrode terminals 58 may be recessed by a distance from 0.01 mm to 1 mm, preferably 0.01 mm to 0.2 mm. In one embodiment of the invention, the electrode terminals are axially adjustable relative to the electrode array surface 82 so that the surgeon can adjust the distance between the surface and the electrode terminals.

The electrode terminals 58 are preferably composed of a refractory, electrically conductive metal or alloy, such as platinum, titanium, tantalum, tungsten and the like. As shown in FIG. 2B, the electrode terminals 58 are anchored in a support matrix 48 of suitable insulating material (e.g., ceramic or glass material, such as alumina, zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point.

Figure 3:
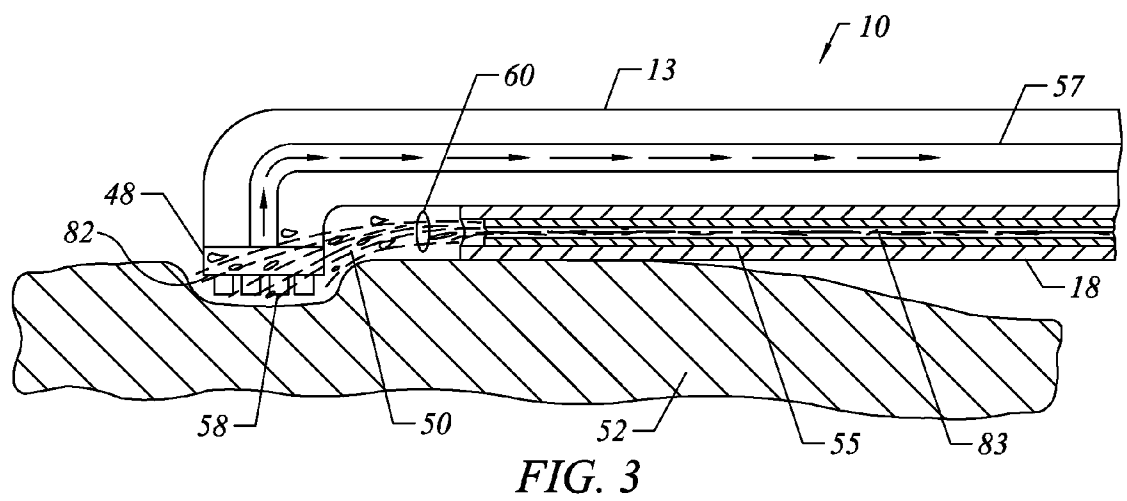
FIG. 3 illustrates an embodiment of a probe where the distal portion of shaft is bent.

As shown in FIG. 2A, the support matrix 48 is adhesively joined to a tubular support member 78 that extends most or all of the distance between matrix 48 and the proximal end of probe 10. Tubular member 78 preferably comprises an electrically insulating material, such as an epoxy, injection moldable plastic or silicone-based material. In a preferred construction technique, electrode terminals 58 extend through pre-formed openings in the support matrix 48 so that they protrude above electrode array surface 82 by the desired distance H (FIG. 3). The electrodes may then be bonded to the distal surface 82 of support matrix 48, typically by an inorganic sealing material 80. Sealing material 80 is selected to provide effective electrical insulation, and good adhesion to both the ceramic matrix 48 and the platinum or titanium electrode terminals. Sealing material 80 additionally should have a compatible thermal expansion coefficient and a melting point well below that of platinum or titanium and alumina or zirconia, typically being a glass or glass ceramic.

In the embodiment shown in FIGS. 2A and 2B, probe 10 includes a return electrode 56 for completing the current path between electrode terminals 58 and power supply 28. Return electrode 56 is preferably an annular member positioned around the exterior of shaft 13 of probe 10. Return electrode 56 may fully or partially circumscribe tubular support member 78 to form an annular gap 54 therebetween for flow of electrically conducting liquid 50 therethrough. Gap 54 preferably has a width in the range of 0.15 mm to 4 mm. Return electrode 56 extends from the proximal end of probe 10, where it is suitably connected to power supply 28 via connectors 19, 20, to a point slightly proximal of electrode array surface 82, typically about 0.5 to 10 mm and more preferably about 1 to 10 mm.

Return electrode 56 is disposed within an electrically insulative jacket 18, which is typically formed as one or more electrically insulative sheaths or coatings, such as polytetrafluoroethylene, polyimide, and the like. The provision of the electrically insulative jacket 18 over return electrode 56 prevents direct electrical contact between return electrode 56 and any adjacent body structure or the surgeon. Such direct electrical contact between a body structure (e.g., tendon) and an exposed common electrode member 56 could result in unwanted heating and necrosis of the structure at the point of contact causing necrosis.

Return electrode 56 is preferably formed from an electrically conductive material, usually metal, which is selected from the group consisting of stainless steel alloys, platinum or its alloys, titanium or its alloys, molybdenum or its alloys, and nickel or its alloys. The return electrode 56 may be composed of the same metal or alloy which forms the electrode terminals 58 to minimize any potential for corrosion or the generation of electrochemical potentials due to the presence of dissimilar metals contained within an electrically conductive fluid 50, such as isotonic saline (discussed in greater detail below).

As shown in FIG. 2A, return electrode 56 is not directly connected to electrode terminals 58. To complete this current path so that terminals 58 are electrically connected to return electrode 56 via target tissue 52, electrically conducting liquid 50 (e.g., isotonic saline) is caused to flow along liquid paths 83. A liquid path 83 is formed by annular gap 54 between outer return electrode 56 and tubular support member 78. An additional fluid transport lumen 57 within an inner tubular member 59 is provided to communicate with a fluid transport apparatus or suction source (such as suction pump 100) via suction lumen 102 and to remove tissue and other material from the treatment site. In some embodiments, fluid transport lumen 57 may optionally be used to supply conductive fluid to a treatment site.

When a voltage difference is applied between electrode array 12 and return electrode 56, high electric field intensities will be generated at the distal tips of terminals 58 with current flow from array 12 through the target tissue to the return electrode, the high electric field intensities causing ablation of tissue 52 in zone 88. Operating parameters of power supply 28 or probe 10 are preferably monitored by controller 104 during operation thereof and suction is applied via suction pump 100 at a desired flow rate and/or pressure to remove the ablated tissue and other material from the treatment site in order to maintain stable plasma field and associated vapor layer conditions.

FIG. 3 illustrates another embodiment of probe 10 where the distal portion of shaft 13 is bent so that electrode terminals extend transversely to the shaft. Preferably, the distal portion of shaft 13 is perpendicular to the rest of the shaft so that electrode surface 82 is generally parallel to the shaft axis, as shown in FIG. 3. In this embodiment, return electrode 55 is mounted to the outer surface of shaft 13 and is covered with an electrically insulating jacket 18. The electrically conducting fluid 50 flows along flow path 83 through return electrode 55 and exits the distal end of electrode 55 at a point proximal of electrode surface 82. The fluid is directed exterior of shaft to electrode surface 82 to create a return current path from electrode terminals 58, through target tissue 52, to return electrode 55, as shown by current flux lines 60 and then removed via transport lumen 57.

Figure 4:
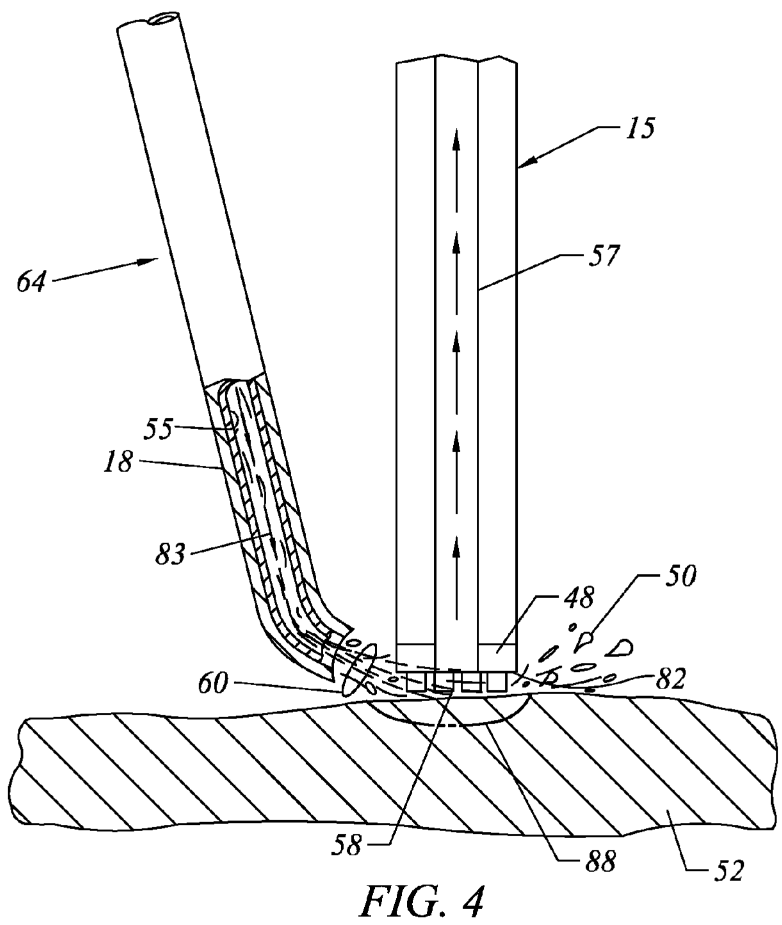
FIG. 4 illustrates an embodiment of a including a separate liquid supply instrument.

FIG. 4 illustrates an embodiment of the invention where electrosurgical system 11 further includes a separate liquid supply instrument 64 for supplying electrically conducting fluid 50 between electrode terminals 58 and return electrode 55. Liquid supply instrument 64 comprises an inner tubular member or return electrode 55 surrounded by an electrically insulating jacket 18. Return electrode 55 defines an inner passage 83 for flow of fluid 50. As shown in FIG. 4, the distal portion of instrument 64 is preferably bent so that liquid 50 is discharged at an angle with respect to instrument 64. This allows the surgical team to position liquid supply instrument 64 adjacent electrode surface 82 with the proximal portion of supply instrument 64 oriented at a similar angle to probe 10. Transport lumen 57 may preferably be used in conjunction with a suction pump and controller to remove ablated tissue from a treatment site at a desired flow rate according to operating parameters indicative of conditions at the distal portion of probe 10.

FIG. 5 illustrates an embodiment of a probe 10 according to the present invention comprising a single active electrode 58 having a tubular geometry. As described above, the return electrode may be an outer tubular member 56 that circumscribes insulated conductor 42 and adhesive bonding material 79 which, in turn, adhesively joins to active electrode support members 48*a* and 48*b*. Electrode support members 48*a* and 48*b* may be ceramic, glass ceramic or other electrically insulating material which resists carbon or arc tracking. A preferred electrode support member material is alumina. In the example embodiment, alumina forms an inner portion 48*b* of electrode support member 48 and a hollow tube of alumina forms an outer portion 48*a* of electrode support member 48. Fluid transport lumen 57 is provided in the interior of inner portion 48*b*. Tubular or ring-shaped active electrode 58 may be fabricated using shaped cylinder of this metal comprising an electrically conductive metal, such as platinum, tantalum, tungsten, molybdenum, columbium or alloys thereof. Active electrode 58 is connected to connector 19 (see FIG. 2C) via an insulated lead 108. An electrically insulating jacket 18 surrounds tubular member 56 and may be spaced from member 56 by a plurality of longitudinal ribs 96 to define an annular gap 54 therebetween (FIG. 22) Annular gap 54 preferably has a width in the range of 0.15 to 4 mm. Ribs 96 can be formed on either jacket 18 or tubular member 56. The distal end of the return electrode 56 is a distance L1 from electrode support surface 82. Distance L1 is preferably about 0.5 mm to 10 mm and more preferably about 1 to 10 mm. The length L1 of return electrode 56 will generally depend on the electrical conductivity of the irrigant solution.

The configuration depicted in FIG. 5 may be used with the integral supply means and return electrodes described above. Alternatively, these probe configuration of FIG. 5 may be operated in body cavities already containing an electrically conducting liquid, obviating the need for either an integral supply of said liquid or an electrically insulating sleeve to form a conduit for supply of the electrically conducting liquid 50. Instead, an electrically insulating covering may be applied to substantially all of the return electrode 56 (other than the proximal portion).

Referring now to FIGS. 6A-6C, an alternative embodiment incorporating a metal screen 610 electrode is illustrated. As shown, metal screen 610 has a plurality of peripheral openings 612 for receiving electrode terminals 1040, and a plurality of inner openings 614 for allowing aspiration of fluid and tissue through opening 609 of the fluid transport lumen. As shown, screen 610 is press fitted over electrode terminals 1040 and then adhered to shaft 1000 of probe 10. In alternate embodiments, metal screen 610 may comprise a mesh-type configuration and may further comprise a variety of conductive metals, such as titanium, tantalum, steel, stainless steel, tungsten, copper, gold or the like.

In one embodiment, during operation of an electrosurgical system utilizing a screen-type electrode, one or more operating parameters may be monitored to determine whether metal screen electrode 610 has become obstructed. Responsive to detecting that screen electrode 610 is obstructed, controller 104 may reverse the flow of suction pump 100 in order to clear the obstruction from screen electrode 610. The monitored operating parameter may include, for instance, pressure within the fluid transport lumen 57.

Figure 7:
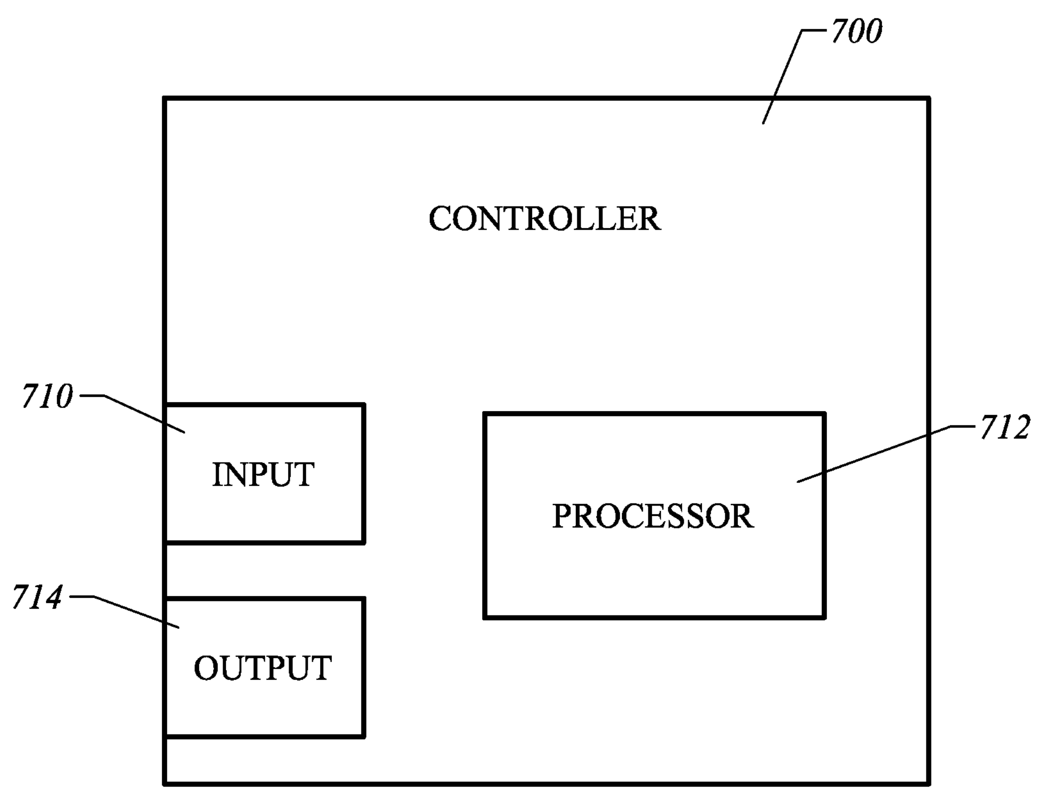
FIG. 7 illustrates a schematic view of an electrosurgical system suction apparatus controller.

Now referring to FIG. 7, a schematic diagram of a controller of the type utilized in the present invention is shown. Controller 700 includes at least one input port 710 and at least one output port 714. Controller 700 preferably receives input from sensors (not expressly shown) within a power supply (such as power supply 28), from a suction lumen (such as fluid transport lumen 57), and/or from an electrosurgical probe (such as probe 10) relating to one or more operating parameters. In a preferred embodiment, the operating parameters may include one or more of the following: impedance, electric current (including whether a treatment current has been initiated or stopped), peak electric current and mean electric current for a selected period, peak electric current and RMS voltage for a selected period. In related embodiments, the operating parameters may include any operating parameters indicative of operating conditions at the treatment surface of the electrosurgical probe and in particular may include operating parameters indicative of the condition of the plasma field or the quality of the vapor layer created proximate the treatment surface. For devices that may operate in more than one operating mode, such as an ablation mode and a coagulation mode, the operating parameter may alternatively include data indicative of the operating mode of the device.

Operating parameter input data indicative of conditions associated with the system received at port 710 is processed by processor 712. Processor 712 may encompass any suitable hardware and software, including controlling logic, necessary to receive the input data and generate desired output commands to provide to a suction source (such as suction pump 100). Output commands generated by processor 712 are sent to a suction source electrically coupled to controller 700 via output port 714. In a preferred embodiment, the output commands generated by processor 712 may include, but are not limited to: dynamically adjust fluid flow through the suction source, initiating fluid flow through the suction source, delay initiating fluid flow through the suction source, ceasing fluid flow through the suction source, decreasing fluid flow through the suction source, incrementally increasing or decreasing fluid flow through the vacuum source, and/or maintain a particular fluid flow through the suction source if the operating parameters remain within a pre-selected value range. In other embodiments, the control signals from controller 700 may dynamically control the pressure at the suction pump. Controller 700 may be a stand-alone device or may be incorporated in a power supply, a suction pump, an electrosurgical device or any combination thereof.

Figure 8:
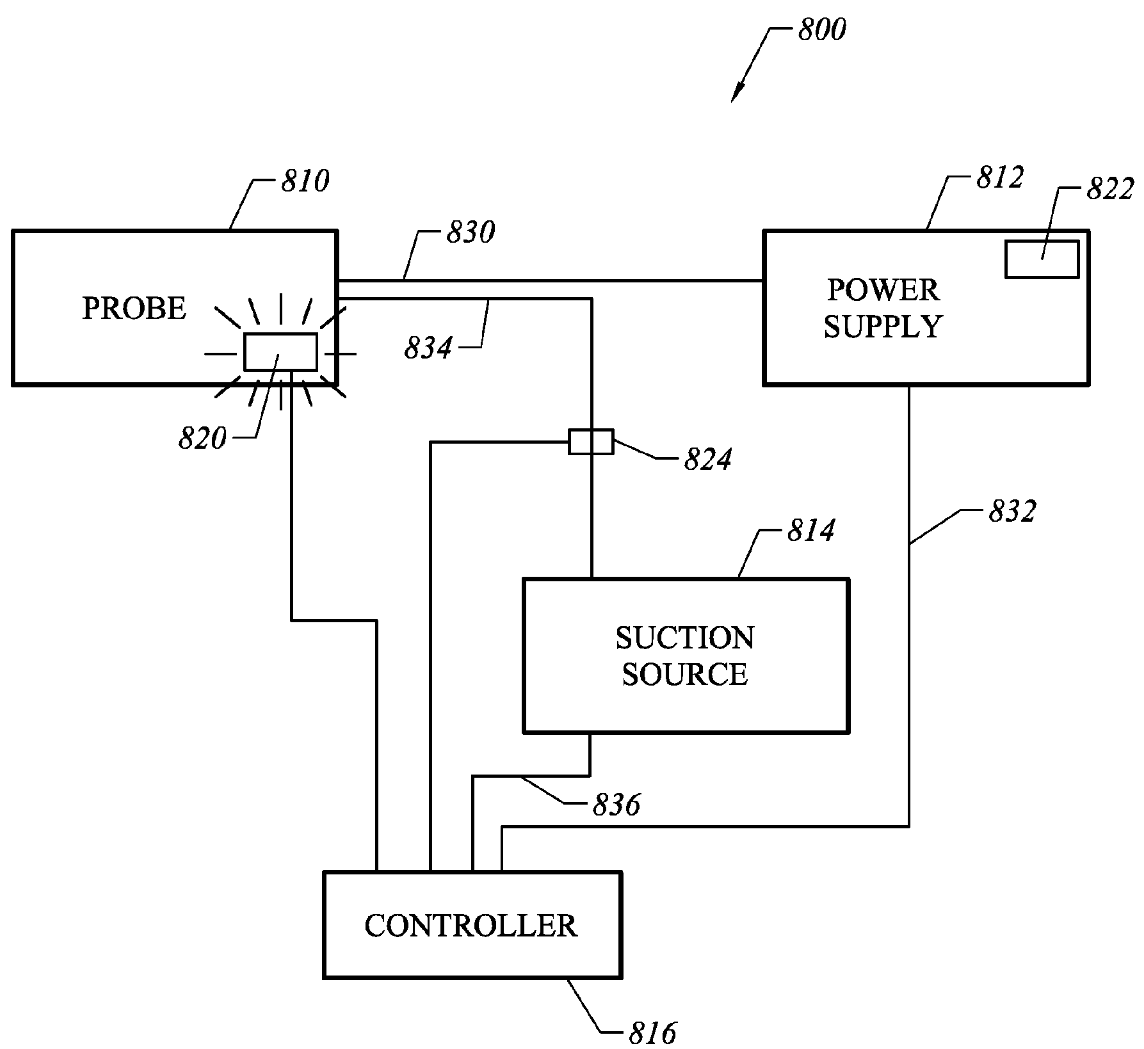
FIG. 8 illustrates a schematic view of an electrosurgical system according to teachings of the present disclosure.

Now referring to FIG. 8, a schematic diagram of an electrosurgical system 800 according to teachings of the present disclosure is shown. Electrosurgical system 800 includes electrosurgical probe 810 which may be any monopolar, bipolar or plasma-based electrosurgical device as discussed above. Probe 810 is in communication with power supply 812 via cable 830 and suction source 814 via suction lumen 834. Optionally, a valve 824 (such as, for example, a pinch valve or other suitable valve) may be provided along suction lumen 834. Controller 816 is in communication with power supply 812 via cable 832 and with suction source 814 via cable 836. Controller 816 is also shown in communication with sensor 820 associated with probe 810, and in communication with valve 824.

Probe sensor 820 is adapted to monitor one or more operating parameters associated with electrosurgical probe 810. Sensor 822 may be associated with power supply 812 and accordingly in communication with controller 816, and is adapted to monitor one or more operating parameters related to power supply 812. In alternate embodiments an additional sensor (not expressly shown) may be provided in association with suction lumen 834 to monitor pressure therein and further to be in communication with controller 816.

In operation, input signals containing one or more selected operating parameters of electrosurgical probe 810 and/or power supply 812 (as discussed above) are preferably sent to controller 816 when probe 810 and power supply 812 are in use. The input signals may be sent from either or both power supply 812, probe 810 or sensors associated therewith (i.e., sensor 820 with respect to probe 810, and sensor 822 with respect to power supply 812). In response to the input signals received, controller 816 may process the data based on the selected operating parameter. Controller 816 may then preferably generate suction source control commands, as discussed above, in response to the received operating parameter input. Controller 816 may then send such suction control commands to suction source 814 via cable 836 to dynamically control suction through lumen 834. In some embodiments, controller 816 may optionally send a control signal to valve device 824 to open or close valve 824. In one alternative embodiment, controller 816 may communicate with probe 810, power supply 812, valve 824 and/or suction source 814 wirelessly.

Although the disclosed embodiments have been described in detail, it should be understood that various changes, substitutions and alterations can be made to the embodiments without departing from their spirit and scope.

What is claimed is:

1. A surgical method for treating tissue using an electrosurgical probe, the electrosurgical probe having a distal end including at least one active electrode, and a fluid transport lumen having an opening proximate the at least one active electrode, the method comprising:

positioning the distal end of the electrosurgical probe adjacent a target tissue;

generating a high frequency voltage between the at least one active electrode and a return electrode;

measuring at least one operating parameter associated with the high frequency voltage delivered by the electrosurgical probe, wherein the at least one operating parameter is indicative of an operating condition;

processing an operating parameter input indicative of the operating condition; and controlling a fluid transport apparatus in communication with the fluid transport lumen based upon the operating parameter input;

wherein controlling the fluid transport apparatus further comprises adjusting a fluid flow through the opening in response to the operating condition to create a desired effect at the at least one active electrode.

2. The method of claim 1 wherein the operating condition is at least one selected from the group consisting of: a status of a generator in communication with the electrosurgical probe; a condition of a plasma field proximate the at least one active electrode; and a condition of a vapor layer proximate the at least one active electrode.

3. The method of claim 2, wherein the condition of the plasma field provides input data indicative of a plasma field stability.

4. The method of claim 2 wherein the status of a generator in communication with the electrosurgical probe is indicative of the activation of the generator.

5. The method of claim 1, wherein generating the high frequency voltage comprises generating a first high frequency voltage at the at least one active electrode in a first operating mode, and controlling the fluid transport apparatus comprises activating the fluid transport apparatus.

6. The method of claim 5, wherein the first operating mode comprises an ablation mode.

7. The method of claim 1, wherein generating the high frequency voltage comprises generating a second high frequency voltage at the at least one active electrode in a second operating mode, and controlling the fluid transport apparatus comprises deactivating the fluid transport apparatus.

8. The method of claim 7, wherein the second operating mode comprises a coagulation mode.

9. The method of claim 1, wherein measuring the at least one operating parameter comprises measuring impedance.

10. The method of claim 1, wherein measuring the at least one operating parameter comprises measuring current.

11. The method of claim 1, wherein controlling the fluid transport apparatus comprises adjusting the fluid flow through the fluid transport apparatus.

12. The method of claim 11, wherein adjusting the fluid flow further comprises dynamically adjusting the fluid flow through the fluid transport apparatus.

13. The method of claim 11, wherein adjusting the fluid flow comprises initiating the fluid flow through the fluid transport apparatus.

14. The method of claim 11, wherein adjusting the fluid flow comprises ceasing the fluid flow through the fluid transport apparatus.

15. The method of claim 11, wherein adjusting the fluid flow comprises decreasing the fluid flow through the fluid transport apparatus.

16. The method of claim 11, wherein adjusting the fluid flow comprises increasing the fluid flow through the fluid transport apparatus.

17. The method of claim 11, wherein adjusting the fluid flow comprises maintaining a preselected fluid flow through the fluid transport apparatus.

18. The method of claim 1, wherein the operating condition is at least one selected from the group consisting of: a condition at the distal end of the electrosurgical probe; and a condition at a treatment surface of the electrosurgical probe.

19. The method of claim 18, wherein the operating condition provides input indicative of the presence of an obstruction at the distal end of the electrosurgical probe.

20. The method of claim 18, wherein the operating condition provides input indicative of a stability of a plasma field at the at least one active electrode.

21. A surgical method for treating tissue using an electrosurgical probe, the electrosurgical probe having a distal end including at least one active electrode, and a fluid transport lumen having an opening proximate the at least one active electrode, the method comprising:

positioning the distal end of the electrosurgical probe adjacent a target tissue;

generating a high frequency voltage between the at least one active electrode and a return electrode;

measuring at least one operating parameter, wherein the at least one operating parameter is indicative of an operating condition;

processing an operating parameter input indicative of the operating condition; and controlling a fluid transport apparatus in communication with the fluid transport lumen based upon the operating parameter input;

wherein controlling the fluid transport apparatus further comprises adjusting a fluid flow through the opening in response to the operating condition to create a desired effect at the at least one active electrode, and wherein the operating condition is at least one selected from the group consisting of: a status of a generator in communication with the electrosurgical probe; a condition of a plasma field proximate the at least one active electrode; and a condition of a vapor layer proximate the at least one active electrode.

22. The method of claim 21, wherein the condition of the plasma field provides input data indicative of a plasma field stability.

23. The method of claim 22, wherein the input data is derived by measuring one of current or impedance at the distal end of the electrosurgical probe.

24. A surgical method for treating tissue using an electrosurgical probe, the electrosurgical probe having a distal end including at least one active electrode, and a fluid transport lumen having an opening proximate the at least one active electrode, the method comprising:

positioning the distal end of the electrosurgical probe adjacent a target tissue;

generating a high frequency voltage between the at least one active electrode and a return electrode;

measuring at least one operating parameter, wherein the at least one operating parameter is indicative of an operating condition;

processing an operating parameter input indicative of the operating condition; and controlling a fluid transport apparatus in communication with the fluid transport lumen based upon the operating parameter input;

wherein controlling the fluid transport apparatus further comprises adjusting a fluid flow through the opening in response to the operating condition to create a desired effect at the at least one active electrode, and wherein the operating condition is at least one selected from the group consisting of: a condition at the distal end of the electrosurgical probe; and a condition at a treatment surface of the electrosurgical probe.

25. The method of claim 24, wherein the operating condition provides input data indicative of the presence of an obstruction at the distal end of the electrosurgical probe.

26. The method of claim 24, wherein the operating condition provides input data indicative of a stability of a plasma field at the at least one active electrode.

27. The method of claim 26, wherein the input data is derived by measuring one of current or impedance at the distal end of the electrosurgical probe.

* * * * *